US010889546B2

United States Patent
You et al.

(10) Patent No.: US 10,889,546 B2
(45) Date of Patent: Jan. 12, 2021

(54) ALKYNYL PYRIDINE PROLYL HYDROXYLASE INHIBITOR, AND PREPARATION METHOD AND MEDICAL USE THEREOF

(71) Applicant: Jiangsu Hengrui Medicine Co., Ltd., Jiangsu (CN)

(72) Inventors: Qidong You, Jiangsu (CN); Xiaojin Zhang, Jiangsu (CN); Yonghua Lei, Jiangsu (CN); Tianhan Hu, Jiangsu (CN); Xingsen Wu, Jiangsu (CN); Haopeng Sun, Jiangsu (CN); Xiaoke Guo, Jiangsu (CN); Xiaoli Xu, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 15/765,387

(22) PCT Filed: Nov. 27, 2015

(86) PCT No.: PCT/CN2015/095728
§ 371 (c)(1),
(2) Date: Apr. 2, 2018

(87) PCT Pub. No.: WO2017/059623
PCT Pub. Date: Apr. 13, 2017

(65) Prior Publication Data
US 2018/0305317 A1    Oct. 25, 2018

(30) Foreign Application Priority Data
Oct. 9, 2015    (CN) .......................... 2015 1 0648342

(51) Int. Cl.
| | | |
|---|---|---|
| C07D 213/81 | (2006.01) | |
| C07D 401/12 | (2006.01) | |
| C07D 405/12 | (2006.01) | |
| A61P 7/06 | (2006.01) | |
| A61K 31/44 | (2006.01) | |
| A61K 31/444 | (2006.01) | |
| A61K 31/4439 | (2006.01) | |
| A61K 31/443 | (2006.01) | |
| A61K 31/551 | (2006.01) | |
| A61K 31/4427 | (2006.01) | |
| A61K 31/4709 | (2006.01) | |
| A61P 7/00 | (2006.01) | |
| A61P 9/10 | (2006.01) | |

(52) U.S. Cl.
CPC ............ *C07D 213/81* (2013.01); *A61K 31/44* (2013.01); *A61K 31/443* (2013.01); *A61K 31/444* (2013.01); *A61K 31/4427* (2013.01); *A61K 31/4439* (2013.01); *A61K 31/4709* (2013.01); *A61K 31/551* (2013.01); *A61P 7/00* (2018.01); *A61P 7/06* (2018.01); *A61P 9/10* (2018.01); *C07D 401/12* (2013.01); *C07D 405/12* (2013.01)

(58) Field of Classification Search
CPC ... C07D 213/81; C07D 401/12; C07D 405/12
See application file for complete search history.

(56) References Cited

U.S. PATENT DOCUMENTS

| | | | |
|---|---|---|---|
| 2007/0299086 A1 | 12/2007 | Kawamoto | |
| 2013/0231323 A1* | 9/2013 | Zhou ..................... | C07C 259/06 514/210.15 |

FOREIGN PATENT DOCUMENTS

| | | |
|---|---|---|
| CN | 101506149 A | 8/2009 |
| CN | 101626685 A | 1/2010 |
| CN | 105130888 A | 12/2015 |
| WO | 2013013609 A1 | 1/2013 |

OTHER PUBLICATIONS

Dikow et al., "How Should We Manage Anaemia in Patients with Diabetes," Nephrol Dial Transplant, vol. 17, Suppl. 1, pp. 67-72 (2002).
Rabinowitz, "Inhibition of Hypoxia-Inducible Factor Prolyl Hydroxylase Domain Oxygen Sensors: Tricking the Body into Mounting Orchestrated Survival and Repair Responses," Journal of Medicinal Chemistry, vol. 56, pp. 9369-9402 (2013).
Vachal et al., "1,3,8-Triazaspiro[4,5]decane-2,4-diones as Efficacious Pan-Inhibitors of Hypoxia-Inducible Factor Prolyl Hydroxylase 1-3 (HIF PHD1-3) for the Treatment of Anemia," Journal of Medicinal Chemistry, vol. 55, pp. 2945-2959 (2012).
Cho et al., "A Fluorescence Polarization-Based Interaction Assay for Hypoxia-Inducible Factor Prolyl Hydroxylases," Biochemical and Biophysical Research Communications, vol. 337, pp. 275-280 (2005).
Hong et al., "[(4-Hydroxyl-benzo[4,5]thieno[3,2-c]pyridine-3-carbonyl)-amino]-acetic Acid Derivatives; HIF prolyl 4-Hydroxylase Inhibitors as Oral Erythropoietin Secretagogues," Bioorganic & Medicinal Chemistry Letters, vol. 23, pp. 5953-5957 (2013).

(Continued)

*Primary Examiner* — Yong S. Chong
(74) *Attorney, Agent, or Firm* — Ice Miller LLP

(57) ABSTRACT

The present invention relates to the field of pharmaceutical chemistry. In particular, the present invention relates to a class of alkynyl pyridine prolyl hydroxylase inhibitors (I). The experiments show that such a compound has good activity of inhibiting prolyl hydroxylase, and can enhance the generation and secretion of erythropoietin in cell or animal models, and thus can promote the generation of red cells, and can be used for the treatment or prevention of anemia, such as chronic kidney disease anemia, and ischemic diseases, including ischemic strokes, myocardial ischemia and other related diseases. The present invention also discloses a method for preparing such a compound.

17 Claims, 1 Drawing Sheet

(56) References Cited

OTHER PUBLICATIONS

Lei et al., "An Improved and Scalable Synthesis of N-(5-(4-cyanophenyl)-3-hydroxypicolinoyl)glycine, a Promising PHD2 Inhibitor for the Treatment of Anemia," Tetrahedron Letters, vol. 56, pp. 5017-5019 (2015).
International Search Report dated Jul. 12, 2016 in International Application No. PCT/CN2015/095728.
Selvaraju et al., "Molecular Mechanisms of Action and Therapeutic Uses of Pharmacological Inhibitors of HIF-Prolyl4-Hydroxylases for Treatment of Ischemic Diseases," Antioxidants & Redox Signaling, vol. 20, No. 16, pp. 2631-2665 (2014).

* cited by examiner

ALKYNYL PYRIDINE PROLYL HYDROXYLASE INHIBITOR, AND PREPARATION METHOD AND MEDICAL USE THEREOF

CROSS-REFERENCE TO RELATED APPLICATION

This application is a Section 371 of International Application No. PCT/CN2015/095728, filed Nov. 27, 2015, which was published in the Chinese language on Apr. 13, 2017, under International Publication No. WO 2017/059623 A1, which claims priority under 35 U.S.C. § 119(b) to Chinese Application No. 201510648342.9, filed Oct. 9, 2015, the disclosures of which are incorporated herein by reference in their entirety.

FIELD OF THE INVENTION

The present invention relates to the field of medicinal chemistry. Specifically, the present invention relates to a class of alkynyl pyridines prolyl hydroxylase inhibitors.

This class of compounds can enhance the production and secretion of erythropoietin, thereby promoting the production of red blood cells, and can be used for the treatment or prevention of anemia, such as anemia in chronic kidney disease, and ischemic diseases, such as ischemic stroke, myocardial ischemia and other related diseases.

BACKGROUND OF THE INVENTION

Anemia generally refers to any abnormality in hemoglobin or red blood cells that leads to reduced oxygen levels in the blood. Anemia can also develop in association with chronic diseases, such as chronic infection, neoplastic diseases, chronic inflammation, including disorders of consequent inflammatory suppression of marrow, etc. Anemia of chronic disease, for example anemia in chronic kidney disease, is one of the most common syndromes in medicine. The main cause of anemia in chronic kidney disease is insufficient secretion of erythropoietin (EPO) (*Nephrol Dial Transplant* 17 (2002)2-7). The insufficient secretion of EPO can hinder the production of red blood cells, resulting in the occurrence of anemia. The expression and secretion of EPO are regulated by the transcription factor hypoxia inducible factor (HIF). The HIF protein with complete transcription function is composed of two subunits HIF-α and HIF-β, in which HIF-α is regulated by prolyl hydroxylase (PHD) that can hydroxylate HIF-α to promote its degradation. Inside the human body, prolyl hydroxylase 2 (PHD2) is the most dominant subtype that regulates HIF levels (*Journal of Medicinal Chemistry* 56 (2013)9369-9402). When the activity of prolyl hydroxylase (PHD) in vivo is inhibited, the HIF-α subunit can be stabilized in vivo, so that it enters the nucleus, and binds to the HIF-β subunit in the nucleus to form a stable HIF dimer.

The dimer further causes the expression of downstream genes, thereby promoting the expression and secretion of EPO. Therefore, the inhibition of activity of prolyl hydroxylase can increase the level of HIF-α and promote the production of EPO, thereby promoting the maturation of red blood cells, enhancing the capacity of blood in delivering oxygen, and improving anemia or ischemic symptoms.

SUMMARY OF THE INVENTION

The present invention provides a small molecule compound that can inhibit the activity of prolyl hydroxylase (PHD). This compound increases the content of HIF-α by inhibiting PHD, thereby increasing the production and secretion of EPO, promoting the maturation of red blood cells, and enhancing the capacity of blood in delivering oxygen. This compound is used for the treatment and prevention of anemia and ischemic diseases, such as anemia in chronic kidney disease, myocardial ischemia, cerebral ischemia, stroke and the like. The structure of the compound of the present invention is as follows:

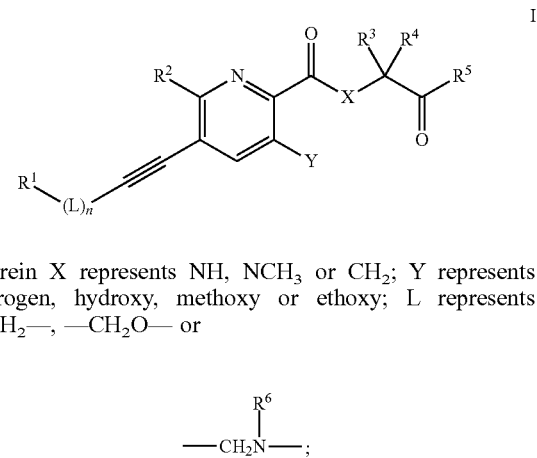

wherein X represents NH, NCH$_3$ or CH$_2$; Y represents hydrogen, hydroxy, methoxy or ethoxy; L represents —CH$_2$—, —CH$_2$O— or

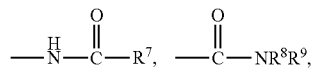

R$^6$ represents hydrogen, C$_1$-C$_4$ alkyl or phenyl; n represents 0 or 1;

R$^1$ represents C$_1$-C$_4$ alkyl, phenyl, substituted phenyl, 5- to 6-membered heteroaryl containing oxygen or nitrogen, substituted 5- to 6-membered heteroaryl containing oxygen or nitrogen, wherein the substituent is C$_1$-C$_4$ alkyl, C$_1$-C$_4$ alkoxy, C$_1$-C$_4$ haloalkyl, halogen, cyano, $$-\underset{H}{N}-\underset{\|}{\overset{O}{C}}-R^7, \quad -\underset{\|}{\overset{O}{C}}-NR^8R^9,$$

phenyl or 5- to 6-membered heteroaryl containing oxygen or nitrogen, wherein R$^7$ represents C$_1$-C$_4$ alkyl; R$^8$ and R$^9$ each independently represents hydrogen or C$_1$-C$_4$ alkyl, or R$^8$ and R$^9$ are attached to form a 3- to 7-membered heterocyclyl containing nitrogen;

R$^2$ represents hydrogen, halogen or methyl; R$^3$ and R$^4$ each independently represents hydrogen, methyl or ethyl; and R$^5$ represents hydroxy, C$_1$-C$_4$ alkoxy or —NR$^{10}$R$^{11}$; R$^{10}$ and R$^{11}$ each independently represents hydrogen, methyl or ethyl.

X preferably represents NH. L preferably represents —CH$_2$—, —CH$_2$O— or

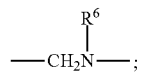

R$^6$ preferably represents hydrogen, methyl, tert-butyl or phenyl. R$^1$ preferably represents substituted phenyl, wherein the substituent is methyl, ethyl, isopropyl, tert-butyl, cyclopropyl, methoxy, tert-butoxy, cyclopropoxy, phenyl, cyano, halogen, fluoromethyl, trifluoromethyl, imidazolyl, acetylamino, cyclopropylcarboxamido or

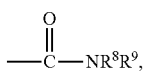

wherein R⁸ and R⁹ each independently represents hydrogen, methyl, butyl or tert-butyl, or R⁸ and R⁹ are attached to form cyclopropylamino, tetrahydropyrrolyl or N-methylhomopiperazinyl.

R¹ also preferably represents cyclopropyl, tert-butyl, phenyl, naphthyl, quinolyl or benzofuranyl.

R³ or R⁴ preferably represents hydrogen. R⁵ preferably represents —NH₂, —NHCH₃, hydroxy, methoxy, isopropoxy, cyclopropoxy or cyclopropylmethoxy.

The present invention also includes a pharmaceutically acceptable salt and a solvate of the compound of formula (I), both of which have the same pharmacological effect as the compound of formula (I).

The present invention discloses a pharmaceutical composition, comprising a compound of formula (I) or a pharmaceutically acceptable salt or solvate thereof, as well as one or more pharmaceutically acceptable carriers, diluents and excipients.

The present invention also provides a use of the compound of formula (I) and/or the pharmaceutically acceptable salt or solvate thereof in the preparation of a medicament for the treatment of a prolyl hydroxylase-mediated disease by inhibiting prolyl hydroxylase. For example, the disease is anemia that can be treated by inhibiting prolyl hydroxylase.

The clinical dose of the compound of the present invention is 0.01-1000 mg/day, and can also deviate from this range according to the severity of the disease or the dosage form.

In certain embodiments, the compound of formula (I) can contain an acidic functional group sufficient to form a salt. Representative salts include a pharmaceutically acceptable metal salt such as sodium, potassium, lithium, calcium, magnesium, aluminum and zinc salts; pharmaceutically acceptable carbonate and bicarbonate of metal cation such as sodium, potassium, lithium, calcium, magnesium, aluminum and zinc; pharmaceutically acceptable salt of organic primary, secondary and tertiary amine, including fatty amine, aromatic amine, fatty diamine and hydroxyalkylamine, such as methylamine, ethylamine, 2-hydroxyethylamine, diethylamine, triethylamine, ethylenediamine, ethanolamine, and diethanolamine.

The present invention also provides a method for preparing formula (I)-related compounds, comprising the following steps of:

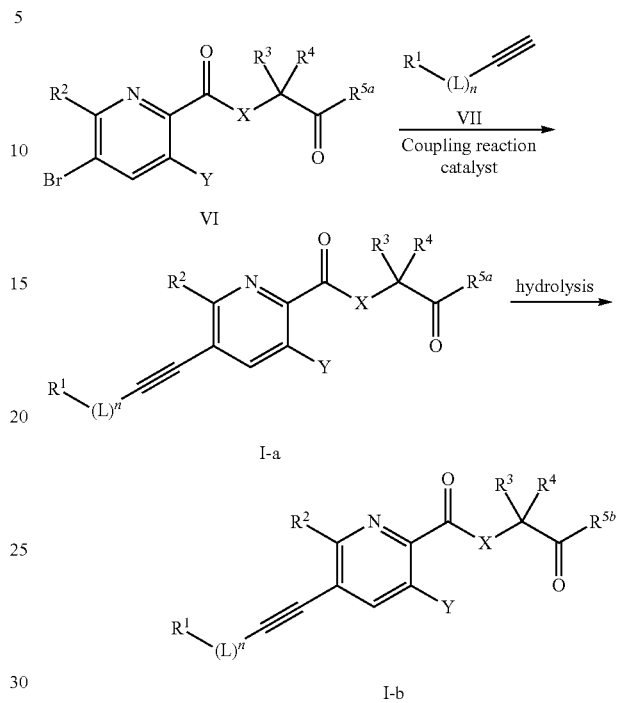

wherein R¹, R², R³, R⁴, X, Y, n and L are as defined previously.

The intermediate VI can be synthesized by the following scheme,

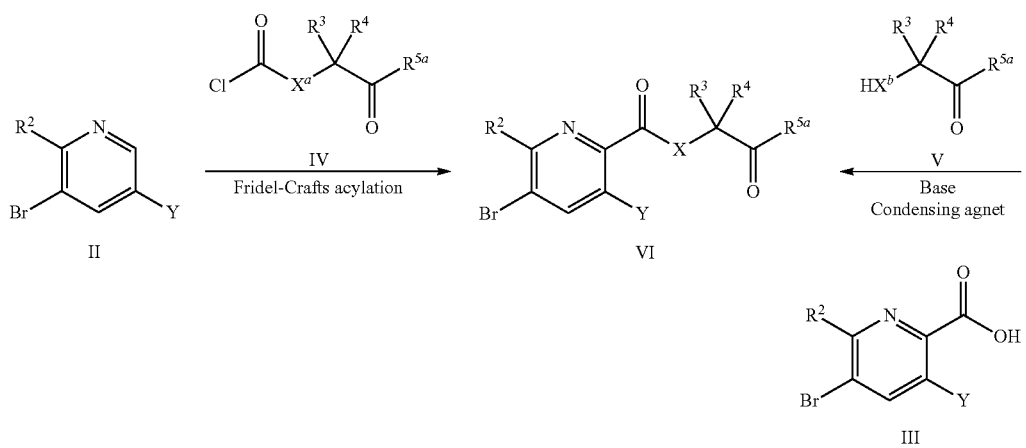

Some of the pharmacodynamic experimental data of the compounds of the present invention are provided below:

The vascular endothelial growth factor (VEGF) and EPO are two markers indicating the increase of HIF in vivo (*Journal of Medicinal Chemistry* 55 (2012)2945-2959). When the activity of PHD is inhibited, the content of HIF in vivo increases. HIF can enter the nucleus to induce the expression of downstream genes, and the expression levels of EPO, VEGF and the like in vivo increase. The compounds were tested for their ability of inhibiting the activity of PHD and increasing HIF at the cellular level by measuring the expression of VEGF and EPO. At the same time, FG-4592 (International Patent Application Publication WO 2013013609A1) is a PHD2 inhibitor for treating anemia that has currently entered the clinical phase III. In the present invention, FG-4592 is used as a positive control compound.

TABLE 1

Prolyl hydroxylase inhibitory activity and related biological activity of some compounds of the present invention

| Number of example compounds | Prolyl hydroxylase 2 ($IC_{50}$ nM) | Whether it can increase the expression of VEGF in cells | Whether it can increase the expression of EPO in cells |
|---|---|---|---|
| 1 | 4530 ± 35.2 | ND | ND |
| 2 | 1423 ± 43 | ND | ND |
| 3 | 1223 ± 56 | Yes | Yes |
| 4 | 834.9 ± 3.2 | Yes | Yes |
| 5 | 820.5 ± 10.9 | Yes | Yes |
| 6 | 5500 ± 43 | Yes | Yes |
| 7 | 215.3 ± 21.0 | ND | Yes |
| 8 | 550.2 ± 12.1 | Yes | Yes |
| 9 | 1045 ± 19.1 | Yes | Yes |
| 10 | 2028.0 ± 4.7 | ND | ND |
| 11 | 1940 ± 23.1 | ND | ND |
| 12 | 2780 ± 44 | ND | ND |
| 13 | 2650 ± 38.2 | ND | ND |
| 14 | 298.3 ± 13.6 | Yes | Yes |
| 15 | 566.7 ± 3.4 | Yes | Yes |
| 16 | 563.7 ± 36.3 | ND | Yes |
| 17 | 463.5 ± 17.0 | Yes | Yes |
| 18 | 8130 ± 40.5 | ND | ND |
| 19 | 310 ± 10.5 | Yes | Yes |
| 20 | 233.9 ± 13.7 | Yes | Yes |
| 21 | 510.4 ± 20.1 | ND | ND |
| 22 | 950.5 ± 18.4 | Yes | Yes |
| 23 | 1055 ± 40.5 | Yes | Yes |
| 24 | 5200 ± 62.2 | ND | Yes |
| 25 | 6211 ± 40.0 | Yes | ND |
| 26 | 2128 ± 34.0 | ND | ND |
| 27 | 1700 ± 87.0 | ND | ND |
| 28 | 125.3 ± 15.5 | Yes | Yes |
| 29 | 3120 ± 47.0 | Yes | Yes |
| 30 | 3756 ± 39.0 | Yes | Yes |
| 31 | 6120 ± 17.5 | ND | ND |
| 32 | 6100 ± 44.0 | ND | ND |
| 33 | 169.5 ± 0.5 | Yes | Yes |
| 34 | 110.1 ± 22.0 | Yes | Yes |
| 35 | 70.4 ± 0.6 | Yes | Yes |
| 36 | 377.9 ± 33.3 | Yes | Yes |
| 37 | 390.5 ± 15.5 | ND | ND |
| 38 | 79.2 ± 1.9 | Yes | Yes |
| 39 | 186.3 ± 3.9 | Yes | Yes |
| 40 | 543.6 ± 9.7 | Yes | Yes |
| 41 | 489.4 ± 31.0 | Yes | Yes |
| 42 | 514.8 ± 6.1 | ND | ND |
| 43 | 402.1 ± 2.2 | ND | ND |
| 44 | 13.7 ± 1.1 | Yes | Yes |
| 45 | 175.1 ± 2.3 | Yes | Yes |
| 46 | 101.8 ± 5.0 | Yes | Yes |
| 47 | 186.6 ± 8.3 | Yes | Yes |
| 48 | 178.2 ± 2.5 | Yes | Yes |
| 49 | 652.6 ± 27.1 | Yes | Yes |
| 50 | 311.1 ± 5.4 | ND | ND |
| 51 | 442.0 ± 6.4 | ND | ND |
| 52 | 310.2 ± 5.7 | ND | Yes |
| 53 | 519.7 ± 3.9 | ND | ND |
| 54 | 210.7 ± 4.4 | Yes | Yes |
| 55 | 220.8 ± 2.9 | Yes | Yes |
| 56 | 689.9 ± 34.0 | ND | ND |
| 57 | 540.0 ± 3.6 | Yes | Yes |
| 58 | 605.5 ± 23.1 | Yes | Yes |
| 59 | 405.2 ± 10.5 | ND | ND |
| 60 | 399.0 ± 3.4 | ND | ND |
| 61 | 527.0 ± 6.1 | Yes | Yes |
| 62 | 449.7 ± 20.4 | Yes | Yes |
| 63 | 759.2 ± 22.1 | ND | Yes |
| 64 | 326.5 ± 0.8 | Yes | Yes |
| 65 | 290.5 ± 7.5 | Yes | Yes |
| 66 | 399.6 ± 1.2 | Yes | Yes |
| 67 | 675.4 ± 7.7 | ND | ND |
| 68 | 1204 ± 23 | ND | ND |
| 69 | 1405 ± 41 | ND | ND |
| FG-4592 | 599.3 ± 13.0 | Yes | Yes |

[a] ND: not determined; [b] the structures of compounds are shown in specific examples; [c] the structure of FG-4592:

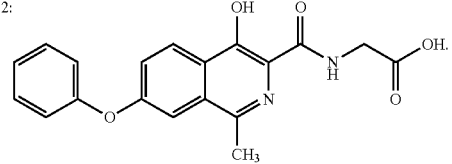

As can be seen from Table 1, the compounds of the present invention have a strong prolyl hydroxylase 2 inhibitory activity.

In addition, patent application US2007/0299086 A1 discloses a series of prolyl hydroxylase inhibitors, wherein the structure of the compound with better activity is:

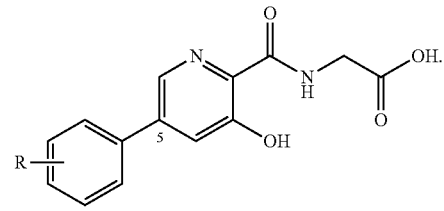

The compound of the present invention is characterized in that an alkynyl group is connected to the 5-position of the pyridine nucleus directly, and the introduction of the alkynyl group at this position can greatly enhance the inhibitory activity of the compound on prolyl hydroxylase. In order to compare the activity of the compounds of the present invention with that of the compounds of US2007/0299086 A1, some of the compounds of patent application US2007/0299086 A1 were synthesized (the synthetic method is described in *Tetrahedron Lett.*, 2015, 56(35), 5017-5019). Prolyl hydroxylase inhibitory activity was evaluated according to the same activity test method of the present invention in the same batch. The comparison results of some of the compounds of the present invention with the compounds of patent application US2007/0299086 are shown as follows:

TABLE 2

Comparison of some of the compounds of the present invention with the compounds of patent application US2007/0299086

| Number and structure of example compounds of the present invention | Prolyl hydroxylase 2 (IC$_{50}$ nM) | Structure of the compounds of patent application US2007/0299086 | Prolyl hydroxylase 2 (IC$_{50}$ nM) |
|---|---|---|---|
| Example 14 [structure] | 298.3 ± 13.6 | [structure] | 2224 ± 20.5 |
| Example 19 [structure] | 377.9 ± 33.3 | [structure] | 1497 ± 43.1 |
| Example 33 [structure] | 169.5 ± 0.5 | [structure] | 2028 ± 33.6 |
| Example 44 [structure] | 13.7 ± 1.1 | [structure] | 1385 ± 53.7 |
| Example 66 [structure] | 399.6 ± 1.2 | [structure] | 1497 ± 43.1 |

It can be seen from the data comparison of the compounds in Table 2 that the introduction of the alkynyl group in the present invention can significantly enhance the inhibitory activity of the compound on prolyl hydroxylase 2 when other groups are substantially the same.

Fluorescence polarization method (*Biochemical and Biophysical Research Communications* 337 (2005) 275-280): The data were read using a fluorescence polarization instrument 1 h after adding the drugs, and the solvent was used as a control.

The inhibition rate of the compounds on prolyl hydroxylase was calculated using the following formula, and the IC$_{50}$ was calculated at the same time. The results are shown in Tables 1 and 3.

In addition to prolyl hydroxylase 2 (PHD2) subtype, prolyl hydroxylase 3 (PHD3) subtype can regulate the content of HIF. Therefore, the representative compounds were also tested for their PHD3 inhibitory activity, and the test results are as follows:

TABLE 3

Inhibitory activity of some compounds of the present invention on prolyl hydroxylase 3

| Number of example | Prolyl hydroxylase 3 (IC$_{50}$ nM) |
|---|---|
| 2 | 805.2 ± 21.6 |
| 7 | 711.0 ± 4.8 |
| 8 | 210.2 ± 3.5 |
| 9 | 675.2 ± 7.8 |
| 11 | 645.2 ± 9.0 |
| 26 | 780.2 ± 22.1 |
| 28 | 99.2 ± 10.2 |
| 40 | 221.0 ± 19.2 |

TABLE 3-continued

Inhibitory activity of some compounds of the present invention on prolyl hydroxylase 3

| Number of example | Prolyl hydroxylase 3 (IC$_{50}$ nM) |
|---|---|
| 41 | 101.2 ± 17.2 |
| 59 | 772.1 ± 30.3 |

The formula is as follows: % inhibition rate=100*(1−(measured value−blank)/(negative value−blank))

As can be seen from Tables 1 and 3, the compounds of the present invention have strong prolyl hydroxylase 2 and 3 inhibitory activity. Among them, the activity of some compounds is significantly better than that of the positive drug FG-4592.

The test of the activity of some compounds of the present invention on VEGF at the cellular level and EPO at the cellular level is shown as follows. The method is in accordance with *Bioorganic & Medicinal Chemistry Letters* 23 (2013) 5953-5957, and the test was carried out by using VEGF and EPO kit respectively 24 h after administration. The results are shown in Table 1.

Hep3B Cell: Human Hepatoma Cell

It can be seen from Table 1 that the compounds of the present invention have the ability to significantly increase the levels of VEGF and EPO in cells, and show good activity at the cellular level.

At the same time, Western-blot test at the cellular level was also carried out for some of the compounds of the present invention. Table 4 shows the experimental results that indicate whether some of the compounds of the present invention have an enhancing effect on the level of HIF-α in cells.

TABLE 4

Whether some of the compounds of the present invention can increase the level of HIF-α in cells

| Number of example | Whether it can increase the level of HIF-α in cells |
|---|---|
| 14 | Yes |
| 15 | Yes |
| 34 | Yes |
| 38 | Yes |
| 44 | Yes |
| 65 | Yes |

At the same time, the results of Western-blot test of some compounds at the cellular level are shown in FIG. 1.

The test of the activity of some compounds of the present invention on VEGF at the animal level and EPO at the cellular level is shown as follows. The method is in accordance with *Journal of Medicinal Chemistry* 55 (2012) 2945-2959, and the test was carried out by using VEGF and EPO kit respectively 4 h after administration. The results are shown in FIG. 2 below.

As can be seen from FIG. 2, the compounds of the present invention can significantly increase the expression of VEGF and EPO at the animal level, indicating that the compounds of the present invention are effective at the animal level.

The alkynyl pyridine compounds of the present invention have good biological activity at the molecular, cellular and animal levels. The compounds of the present invention can increase the level of erythropoietin (EPO) in blood at the animal level, thereby promoting the production of red blood cells, and can be used for the treatment or prevention of anemia related to chronic diseases, ischemic diseases and hematopoietic system-related diseases.

DETAILED DESCRIPTION OF THE INVENTION

Example 1

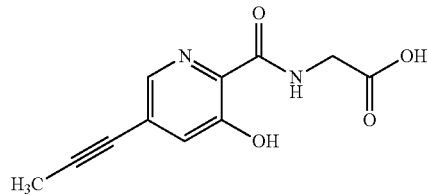 [SMILES: CC#Cc1cnc(C(=O)NCC(=O)O)c(O)c1]

2-(3-Hydroxy-5-propynyl)picolinamido acetic acid

1) Preparation of methyl 2-(3-hydroxy-5-bromopyridine)carboxamido acetate

Figure 1:
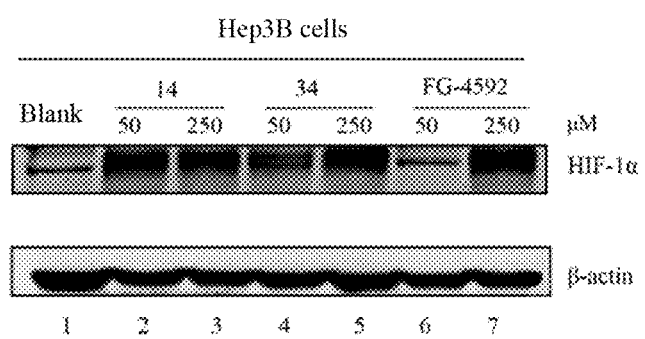
FIG. 1 is the results of Western-blot test of some compounds at the cellular level (Hep3B cell: human hepatoma cell; the compound concentration: 50 μM, 250 μM, 24 hours after administration)
Figure 2:
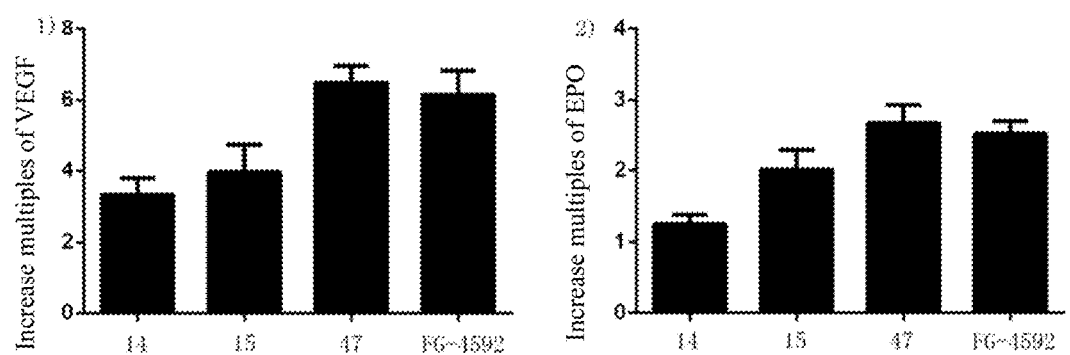
FIG. 2 is the test of increased level of VEGF and EPO in cells 24 h after the administration of compounds 14, 15, 47 and FG-4592 at a concentration of 50 μM (model: C57Bl/6 mice, male, 8-9 weeks old)

Compound III 3-hydroxy-5-bromopicolinic acid (3.47 g, 16 mmol) was dissolved in 150 mL of dichloromethane, then 7.3 mL of triethylamine and HOBt (3.26 g, 24 mmol) were added. EDCI (4.59 g, 24 mmol) was added after the mixture was stirred for 10 min. Glycine methyl ester hydrochloride (2.4 g, 19.2 mmol) was added after the mixture was stirred for 10 min. The mixture was stirred for 6 h at room temperature. The mixture was washed successively with saturated sodium bicarbonate (100 mL), water (2×100 mL) and saturated brine (2×100 mL). The mixture was dried over anhydrous sodium sulfate, and concentrated under reduced pressure. The crude product was purified by silica gel column chromatography (petroleum ether:ethyl acetate=3:1) to obtain a white solid compound (1.88 g, yield: 65.3%). m.p. 143.6-145.7° C. 1H-NMR (300 MHz, CDCl$_3$) δ 11.90 (s, 1H), 8.16 (s, 1H), 7.54 (d, J=1.83 Hz, 1H), 7.28 (d, J=1.86 Hz, 1H), 4.25 (d, J=3.3 Hz, 2H), 3.83 (s, 3H); EI-MS m/z: 288/290[M]$^+$.

2) Preparation of methyl 2-(3-hydroxy-5-propynyl)picolinamido acetate

The compound methyl 2-(3-hydroxy-5-bromopyridine)carboxamido acetate (288 mg, 1 mmol) and propyne (44 mg, 1.1 mmol) were dissolved in 6 mL of DMF, then 6 mL of N,N-diisopropylethylamine, 40 mg of cuprous iodide, and 40 mg of dichloro(bis(triphenylphosphine))palladium were added. The mixture was heated to 80° C. by a conventional method for 6 h, or heated to 80° C. by microwave for 15 min, and the reaction was substantially completed. After the completion of the reaction, 100 mL of dichloromethane and 60 mL of hydrochloric acid (3 mmol) were added. After separation, the solution was washed successively with water (2×100 mL) and saturated brine (2×100 mL). The solution was dried over anhydrous sodium sulfate, and concentrated under reduced pressure. The crude product was purified by silica gel column chromatography (petroleum ether:ethyl acetate=6:1) to obtain a white solid compound (124.5 mg, yield: 50.2%). m.p. 119.2-121.5° C. $^1$H-NMR (300 MHz, CDCl$_3$) δ 8.91 (s, 1H), 8.76 (d, J=1.2 Hz, 1H), 8.20 (s, 1H), 7.69 (d, J=1.2 Hz, 1H), 3.92 (s, 2H), 3.64 (s, 3H), 1.85 (s, 3H); EI-MS m/z: 248[M]$^+$.

3) Preparation of the title compound 2-(3-hydroxy-5-propynyl)picolinamido acetic acid Methyl 2-(3-hydroxy-5-propynyl)picolinamido acetate (100.0 mg, 0.4 mmol) was dissolved in 10 mL of tetrahydrofuran, then 3 mL of 1 M lithium hydroxide was added. The mixture was heated to 30° C. for 3 h to complete the reaction. After the completion of the reaction, tetrahydrofuran in the reaction solution was removed by pressurized distillation, then 3 mmol of dilute hydrochloric acid was added in an ice bath to precipitate a white solid. The white solid was filtered and dried to obtain a white product (61.0 mg, yield: 65.2%). m.p. 179.1-181.3° C. $^1$H-NMR (300 MHz, DMSO-d$_6$) δ 8.91 (s, 1H), 8.76 (d, J=1.2 Hz, 1H), 8.20 (s, 1H), 7.70 (d, J=1.3 Hz, 1H), 3.60 (s, 2H), 1.85 (s, 3H); EI-MS m/z: 234[M]$^+$.

Example 2

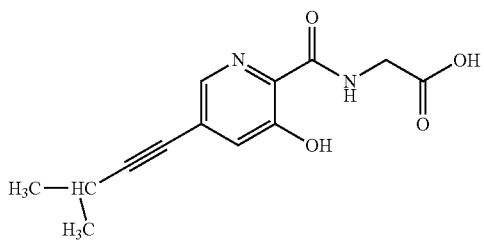 [SMILES: CC(C)C#Cc1cnc(C(=O)NCC(=O)O)c(O)c1]

2-(3-Hydroxy-5-isopropylethynyl)picolinamido acetic acid

In accordance with the method of Example 1, propyne was replaced by isopropylacetylene (74.8 mg, 1.1 mmol). Accordingly, a white solid product was obtained (112.0 mg, yield of two steps: 42.7%). m.p. 155.5-157.8° C. $^1$H-NMR (300 MHz, DMSO-d$_6$) δ 8.91 (s, 1H), 8.79 (d, J=1.2 Hz, 1H), 8.20 (s, 1H), 7.70 (d, J=1.2 Hz, 1H), 3.60 (s, 2H), 2.89-2.85 (m, 1H), 1.26 (d, J=6.8 Hz, 6H); EI-MS m/z: 262[M]$^+$.

Example 3

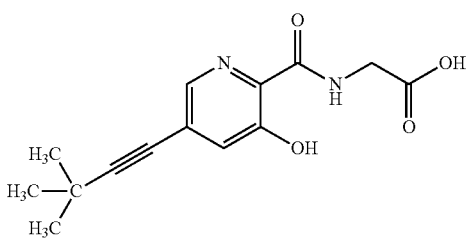 [SMILES: CC(C)(C)C#Cc1cnc(C(=O)NCC(=O)O)c(O)c1]

2-(3-Hydroxy-5-tert-butylethynyl)picolinamido acetic acid

In accordance with the method of Example 1, propyne was replaced by tert-butylacetylene (90.2 mg, 1.1 mmol). Accordingly, a white solid compound was obtained (98.0 mg, yield of two steps: 35.5%). m.p. 165.2-167.8° C. $^1$H NMR (300 MHz, DMSO-d$_6$) δ 8.78 (d, J=1.2 Hz, 1H), 8.20 (s, 1H), 7.69 (d, J=1.2 Hz, 1H), 3.60 (s, 2H), 1.27 (s, 9H); EI-MS m/z: 276[M]$^+$.

Example 4

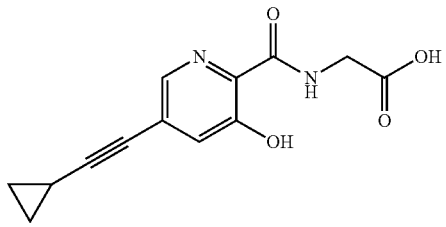 [SMILES: O=C(O)CNC(=O)c1ncc(C#CC2CC2)cc1O]

2-(3-Hydroxy-5-cyclopropylethynyl)picolinamido acetic acid

In accordance with the method of Example 1, propyne was replaced by cyclopropylacetylene (72.6 mg, 1.1 mmol). Accordingly, a white solid compound was obtained (79.1 mg, yield of two steps: 30.42%). m.p. 154.2-155.4° C. $^1$H NMR (300 MHz, DMSO-d$_6$) δ 8.68 (d, J=1.3 Hz, 1H), 8.20 (s, 1H), 7.63 (d, J=1.3 Hz, 1H), 3.60 (s, 2H), 1.41-1.32 (m, 1H), 0.63-0.44 (m, 2H), 0.45-0.25 (m, 2H); EI-MS m/z: 261[M]$^+$.

Example 5

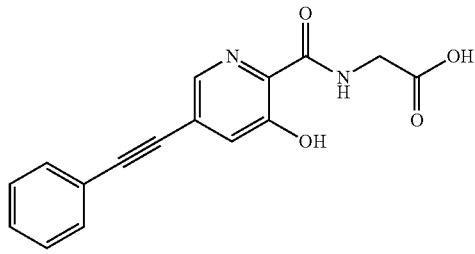 [SMILES: O=C(O)CNC(=O)c1ncc(C#Cc2ccccc2)cc1O]

2-(3-Hydroxy-5-phenylethynyl)picolinamido acetic acid

In accordance with the method of Example 1, propyne was replaced by phenylacetylene (112.2 mg, 1.1 mmol). Accordingly, a white solid compound was obtained (102.2 mg, yield of two steps: 34.4%). m.p. 172.1-173.9° C. $^1$HNMR (300 MHz, DMSO-d$_6$) δ8.75 (d, J=1.2 Hz, 1H), 8.20 (s, 1H), 7.68 (d, J=1.3 Hz, 1H), 7.60-7.49 (m, 2H), 7.48-7.27 (m, 3H), 3.89 (s, 2H); EI-MS m/z: 296[M]$^+$.

Example 6

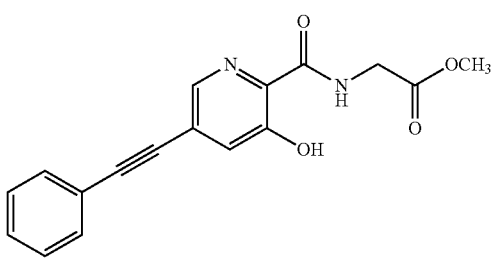 [SMILES: COC(=O)CNC(=O)c1ncc(C#Cc2ccccc2)cc1O]

Methyl 2-(3-hydroxy-5-phenylethynyl)picolinamido acetate

Methyl 2-(3-hydroxy-5-bromopyridine)carboxamido acetate (288 mg, 1 mmol) and phenylacetylene (110.2 mg, 1.1 mmol) were dissolved in 6 mL of DMF, then 6 mL of N,N-diisopropylethylamine, 40 mg of cuprous iodide, and 40 mg of dichloro(bis(triphenylphosphine))palladium were added. The mixture was heated to 80° C. by a conventional method for 6 h, or heated to 80° C. by microwave for 15 min, and the reaction was substantially completed. After the completion of the reaction, 100 mL of dichloromethane and 60 mL of hydrochloric acid (3 mmol) were added. After separation, the solution was washed successively with water (2×100 mL) and saturated brine (2×100 mL). The solution was dried over anhydrous sodium sulfate, and concentrated under reduced pressure. The crude product was purified by silica gel column chromatography (petroleum ether:ethyl acetate=6:1) to obtain a white solid compound (140.0 mg, yield: 45.2%). m.p. 109.7-111.9° C. $^1$HNMR (300 MHz, DMSO-$d_6$) δ 8.77 (d, J=1.2 Hz, 1H), 8.20 (s, 1H), 7.69 (d, J=1.2 Hz, 1H), 7.60-7.49 (m, 2H), 7.48-7.27 (m, 3H), 3.92 (s, 2H), 3.64 (s, 3H); EI-MS m/z: 310[M]$^+$.

Example 7

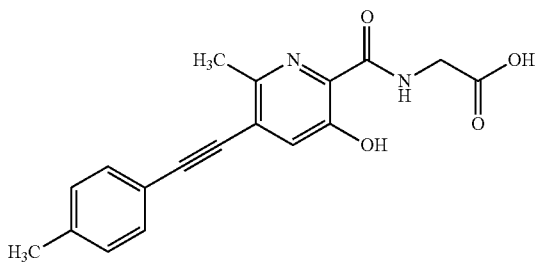 [SMILES: Cc1ccc(C#Cc2cc(O)c(C(=O)NCC(=O)O)nc2C)cc1]

2-(3-Hydroxy-5-p-methylphenylethynyl-6-methyl) picolinamido acetic acid

In accordance with the method of Example 1, 3-hydroxy-5-bromopicolinic acid was replaced by 3-hydroxy-5-bromo-6-methylpicolinic acid (372 mg, 2 mmol), and propyne was replaced by p-methylphenylacetylene (127.6 mg, 1.1 mmol). Accordingly, a white solid product was obtained (120.3 mg, yield of three steps: 18.5%). m.p. 223.3-225.6° C. $^1$H NMR (300 MHz, DMSO-$d_6$) δ 8.20 (s, 1H), 7.67 (s, 1H), 7.51-7.40 (m, 2H), 7.01-7.17 (m, 1.1 Hz, 2H), 3.88 (s, 2H), 2.73 (s, 3H), 2.34 (t, J=1.1 Hz, 3H); EI-MS m/z: 324[M]$^+$.

Example 8

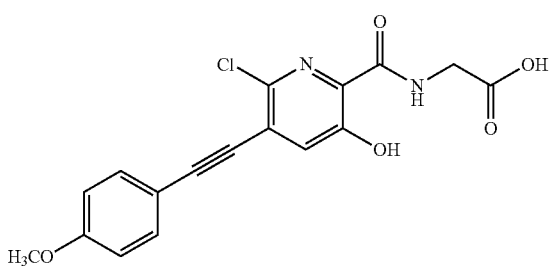 [SMILES: COc1ccc(C#Cc2cc(O)c(C(=O)NCC(=O)O)nc2Cl)cc1]

2-(3-Hydroxy-5-p-methoxyphenylethynyl-6-chloro) picolinamido acetic acid

In accordance with the method of Example 1, 3-hydroxy-5-bromopicolinic acid was replaced by 3-hydroxy-5-bromo-6-chloropicolinic acid (412 mg, 2 mmol), and propyne was replaced by p-methoxyphenylacetylene (145.2 mg, 1.1 mmol), accordingly, a light yellow solid product was obtained (127.0 mg, yield of three steps: 17.6%). m.p. 232.2-234.3° C. $^1$H NMR (300 MHz, DMSO-$d_6$) (8.20 (s, 1H), 7.85 (s, 1H), 7.51-7.40 (m, 2H), 7.00-6.89 (m, 2H), 3.80 (s, 3H), 3.60 (s, 2H); EI-MS m/z: 360[M]$^+$.

Example 9

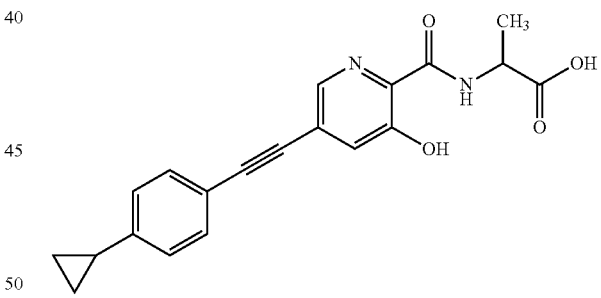

2-(3-Hydroxy-5-p-cyclopropylphenylethynylpyridine)carboxamido propionic acid

In accordance with the method of Example 1, glycine methyl ester hydrochloride was replaced by alanine methyl ester hydrochloride, and propyne was replaced by p-cyclopropylphenylacetylene (156.2 mg, 1.1 mmol). Accordingly, a white solid product was obtained (77 mg, yield of two steps: 22.0%). m.p. 202.5-204.7° C. $^1$H NMR (300 MHz, DMSO-$d_6$) (8.85 (d, J=1.2 Hz, 1H), 7.74 (d, J=1.2 Hz, 1H), 7.57-7.46 (m, 2H), 7.20-7.04 (m, 3H), 4.31-4.40 (m, =1H), 1.94-1.77 (m, 1H), 1.42 (d, J=6.8 Hz, 3H), 1.21-1.06 (m, 2H), 0.82-0.90 (m, 2H); EI-MS m/z: 350[M]$^+$.

Example 10

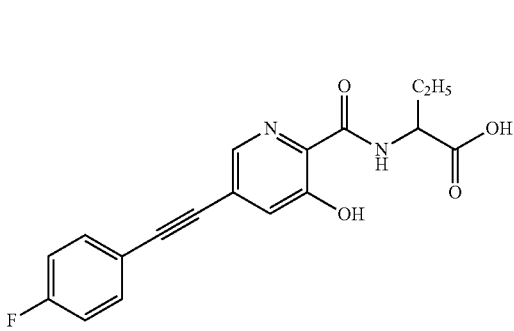 [SMILES: CCC(NC(=O)c1ncc(C#Cc2ccc(F)cc2)cc1O)C(=O)O]

2-(3-Hydroxy-5-p-fluorophenylethynylpyridine) carboxamido butyric acid

In accordance with the method of Example 1, glycine methyl ester hydrochloride was replaced by methyl aminobutanoate hydrochloride, and propyne was replaced by p-fluorophenylacetylene (149.6 mg, 1.1 mmol), accordingly, a light yellow solid product was obtained (145 mg, yield of two steps: 40.5%). m.p. 177.6-179.9° C. $^1$H NMR (300 MHz, DMSO-d$_6$) (8.77 (d, J=1.2 Hz, 1H), 7.69 (d, J=1.3 Hz, 1H), 7.58-7.48 (m, 2H), 7.46-7.35 (m, 2H), 7.08 (s, 1H), 4.60 (d, J=1.4 Hz, 1H), 2.11-1.82 (m, 2H), 1.02 (t, J=6.0 Hz, 3H). EI-MS m/z: 342[M]$^+$.

Example 11

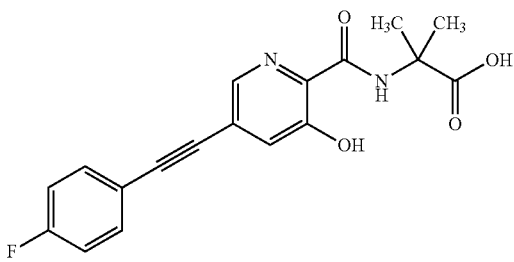 [SMILES: CC(C)(NC(=O)c1ncc(C#Cc2ccc(F)cc2)cc1O)C(=O)O]

2-(3-Hydroxy-5-p-fluorophenylethynylpyridine) carboxamido butyric acid

In accordance with the method of Example 1, glycine methyl ester hydrochloride was replaced by methyl aminoisobutanoate hydrochloride, and propyne was replaced by p-fluorophenylacetylene (149.6 mg, 1.1 mmol). Accordingly, a light yellow solid product was obtained (115 mg, yield of two steps: 32.12%). m.p. 175.4-177.5° C. $^1$H NMR (300 MHz, DMSO-d$_6$) δ 8.94 (s, 1H), 8.75 (d, J=1.2 Hz, 1H), 7.67 (d, J=1.3 Hz, 1H), 7.58-7.47 (m, 2H), 7.45-7.35 (m, 2H), 1.55 (s, 6H). EI-MS m/z: 342[M]$^+$.

Example 12

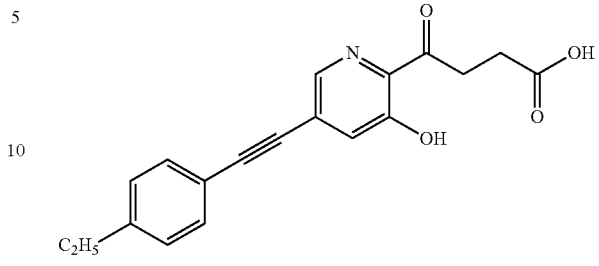

4-(3-Hydroxy-5-(4-ethylphenylalkynyl))pyridine-4-oxobutanoic acid (1) Preparation of methyl 4-(3-hydroxy-5-bromopyridin-2-yl)-4-oxobutanoate 3-Hydroxy-5-bromopyridine (348 mg, 2 mmol) was dissolved in 40 mL of dichloromethane, then methyl succinyl chloride (400 mg, 4 mmol) and 100 mg of aluminum trichloride were added in an ice bath. The reaction was carried out at room temperature for 2 hours. After the completion of the reaction, water and 3 M hydrochloric acid were added. After separation, the solution was washed successively with (2×100 mL) and saturated brine (1×100 mL). The solution was dried over anhydrous sodium sulfate, and concentrated under reduced pressure. The crude product was purified by silica gel column chromatography (petroleum ether:ethyl acetate=5:1) to obtain a white solid compound (196.5 mg, yield: 34.1%). m.p. 156.6-158.2° C. $^1$H NMR (300 MHz, CDCl$_3$) δ 8.64 (d, J=1.3 Hz, 1H), 7.77 (d, J=1.3 Hz, 1H), 3.63 (s, 3H), 3.05 (t, J=7.1 Hz, 2H), 2.78 (t, J=7.0 Hz, 2H). EI-MS m/z: 287[M]$^+$.

(2) Preparation of methyl 4-(3-hydroxy-5-p-ethylphenylalkynylpyridine-2-yl)-4-oxobutanoate Methyl 4-(3-hydroxy-5-bromopyridin-2-yl)-4-oxobutanoate (190 mg, 0.66 mmol) and p-ethylphenylacetylene (94 mg, 0.72 mmol) were dissolved in 6 mL of DMF, then 6 mL of N,N-diisopropylethylamine, 40 mg of cuprous iodide, and 40 mg of dichloro(bis(triphenylphosphine))palladium were added. The mixture was heated to 80° C. by a conventional method for 6 h, or heated to 80° C. by microwave for 15 min, and the reaction was substantially completed. After the completion of the reaction, 100 mL of dichloromethane and 60 mL of hydrochloric acid (3 mmol) were added. After separation, the solution was washed successively with water (2×100 mL) and saturated brine (2×100 mL). The solution was dried over anhydrous sodium sulfate, and concentrated under reduced pressure. The crude product was purified by silica gel column chromatography (petroleum ether:ethyl acetate=6:1) to obtain a white solid compound (84.5 mg, yield: 38.1%). m.p. 109.5-112.1° C. $^1$H NMR (300 MHz, CDCl$_3$) δ 8.76 (d, J=1.2 Hz, 1H), 7.63 (d, J=1.3 Hz, 1H), 7.57-7.46 (m, 2H), 7.20-7.06 (m, 2H), 3.63 (s, 3H), 2.84-2.64 (m, 4H), 2.58 (t, J=5.7 Hz, 2H), 1.19 (t, J=6.6 Hz, 3H). EI-MS m/z: 337[M]$^+$.

(3) Preparation of the Title Compound 4-(3-hydroxy-5-(4-ethylphenylalkynyl))pyridine-4-oxobutanoic acid Methyl 2-(3-hydroxy-5-propynyl)picolinamido acetate (70.0 mg, 0.2 mmol) was dissolved in 10 mL of tetrahydrofuran, then 3 mL of 1 M lithium hydroxide was added. The mixture was heated to 30° C. for 3 h to complete the reaction. After completion of the reaction, tetrahydrofuran in the reaction solution was removed by pressurized distillation, then 3 mmol of dilute hydrochloric acid was added in an ice bath to precipitate a white solid. The white solid was filtered and dried to obtain a white product (41.0 mg, yield: 56.9%). m.p. 185.7-187.8° C. $^1$H NMR (300 MHz, DMSO-$d_6$) δ 8.77 (d, J=1.2 Hz, 1H), 7.64 (d, J=1.2 Hz, 1H), 7.57-7.46 (m, 2H), 7.20-7.17 (m, 2H), 2.87 (t, J=5.4 Hz, 2H), 2.78-2.62 (m, 4H), 1.19 (t, J=6.6 Hz, 3H). EI-MS m/z: 358[M]$^+$.

Example 13

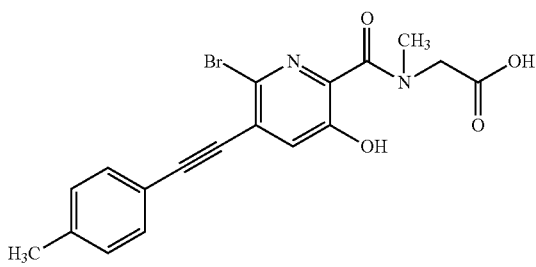 [SMILES: Cc1ccc(C#Cc2cc(O)c(C(=O)N(C)CC(=O)O)nc2Br)cc1]

N-(6-Bromo-5-p-methylphenylethynyl-3-hydroxy-2-pyridyl)formyl-N-methylglycine

In accordance with the method of Example 1, glycine methyl ester hydrochloride, propyne, and 5-bromo-3-hydroxypicolinic acid were respectively replaced by N-methylglycine methyl ester hydrochloride (333.2 mg, 2.4 mmol), p-methylphenylacetylene (255.2 mg, 2.2 mmol), and 5,6-dibromo-3-hydroxypicolinic acid (592 mg, 2 mmol). Accordingly, a light yellow solid product was obtained after hydrolysis (121.0 mg, yield of three steps: 15.1%). m.p. 227.1-229.4° C. $^1$H NMR (300 MHz, DMSO-$d_6$) δ 7.79 (s, 1H), 7.55-7.44 (m, 2H), 7.12-7.09 (m, 2H), 3.90 (s, 2H), 3.05 (s, 3H), 2.34 (s, 2H), 2.34 (d, J=2.3 Hz, 1H). EI-MS m/z: 402/404[M]$^+$.

Example 14

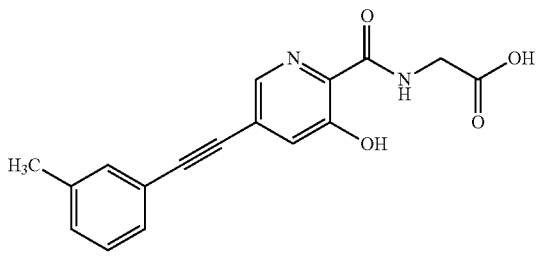 [SMILES: Cc1cccc(C#Cc2cnc(C(=O)NCC(=O)O)c(O)c2)c1]

2-(3-Hydroxy-5-m-methylphenylethynyl)picolinamido acetic acid

The preparation method is the same as that of Example 1, and propyne was replaced by m-methylphenylacetylene (127.6 mg, 1.1 mmol). Accordingly, a white solid product was obtained (106.0 mg, yield of three steps: 34.2%). m.p. 229.2-231.3° C. $^1$H NMR (300 MHz, DMSO-$d_6$) δ 8.75 (d, J=1.3 Hz, 1H), 8.20 (s, 1H), 7.67 (d, J=1.2 Hz, 1H), 7.54-7.43 (m, 2H), 7.15-7.05 (m, 2H), 3.60 (s, 2H), 2.34 (d, J=1.1 Hz, 3H). EI-MS m/z: 310[M]$^+$.

Example 15

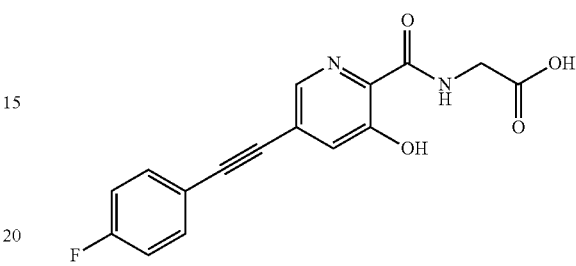

2-(3-Hydroxy-5-p-fluorophenylethynyl)picolinamido acetic acid

The preparation method is the same as that of Example 1, and propyne was replaced by p-fluorophenylacetylene (132.0 mg, 1.1 mmol). Accordingly, a white solid product was obtained (112.4 mg, yield of three steps: 36.1%). m.p. 187.8-200.7° C. $^1$H NMR (300 MHz, DMSO-$d_6$) δ 8.75 (d, J=1.3 Hz, 1H), 8.20 (s, 1H), 7.69-7.52 (m, 3H), 7.13-6.99 (m, 2H), 3.60 (s, 2H). EI-MS m/z: 314[M]$^+$.

Example 16

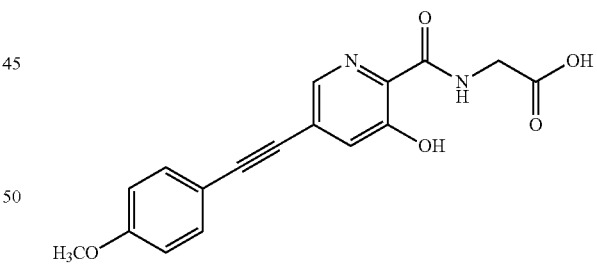

2-(3-Hydroxy-5-p-methoxyphenylethynyl)picolinamido acetic acid

The preparation method is the same as that of Example 1, and propyne was replaced by p-methoxyphenylacetylene (145.2 mg, 1.1 mmol). Accordingly, a white solid product was obtained (142.4 mg, yield of three steps: 43.5%). m.p. 219.2-221.3° C. $^1$H NMR (300 MHz, DMSO-$d_6$) δ 8.73 (d, J=1.2 Hz, 1H), 8.20 (s, 1H), 7.67 (d, J=1.2 Hz, 1H), 7.50-7.39 (m, 2H), 7.00-6.89 (m, 2H), 3.80 (s, 3H), 3.60 (s, 2H). EI-MS m/z: 326[M]$^+$.

Example 17

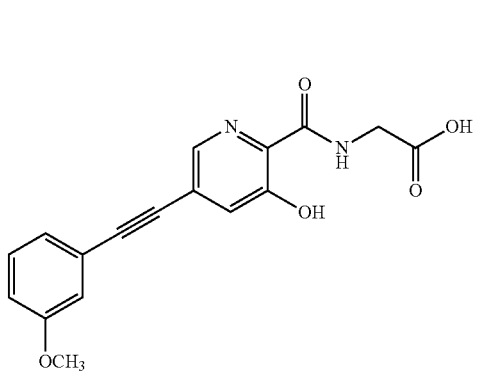 [SMILES: COc1cccc(C#Cc2cnc(C(=O)NCC(=O)O)c(O)c2)c1]

2-(3-Hydroxy-5-m-methoxyphenylethynyl)picolinamido acetic acid

The preparation method is the same as that of Example 1, and propyne was replaced by m-methoxyphenylacetylene (145.2 mg, 1.1 mmol). Accordingly, a light yellow solid product was obtained (92.4 mg, yield of three steps: 28.3%). m.p. 220.2-222.5° C. $^1$H NMR (300 MHz, DMSO-d$_6$) δ 8.77 (d, J=1.3 Hz, 1H), 8.20 (s, 1H), 7.67 (d, J=1.2 Hz, 1H), 7.29 (t, J=7.4 Hz, 1H), 7.24-7.08 (m, 2H), 6.95-6.91 (m, 1H), 3.81 (s, 3H), 3.60 (s, 2H). EI-MS m/z: 326[M]$^+$.

Example 18

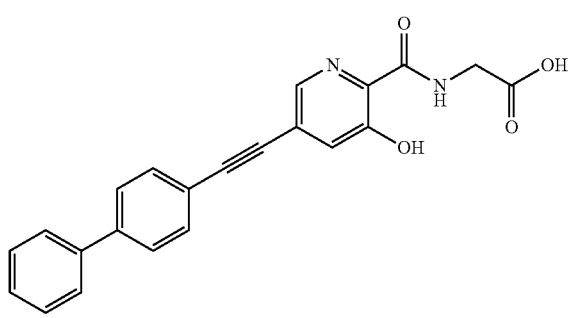 [SMILES: O=C(O)CNC(=O)c1ncc(C#Cc2ccc(-c3ccccc3)cc2)cc1O]

2-(3-Hydroxy-5-(biphenyl-4-ylethynyl))picolinamido acetic acid

The preparation method is the same as that of Example 1, and propyne was replaced by biphenylacetylene (195.8 mg, 1.1 mmol). Accordingly, a brown solid product was obtained (82.2 mg, yield of three steps: 22.1%). m.p. 242.5-244.3° C. $^1$H NMR (300 MHz, DMSO-d$_6$) δ 8.87 (d, J=1.2 Hz, 1H), 8.20 (s, 1H), 7.81-7.69 (m, 3H), 7.67-7.53 (m, 4H), 7.51-7.37 (m, 2H), 7.39-7.26 (m, 1H), 3.60 (s, 2H). EI-MS m/z: 372[M]$^+$.

Example 19

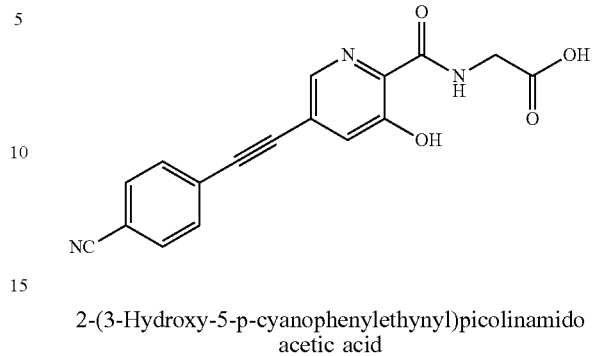

2-(3-Hydroxy-5-p-cyanophenylethynyl)picolinamido acetic acid

The preparation method is the same as that of Example 1, and propyne was replaced by p-cyanophenylacetylene (139.7 mg, 1.1 mmol). Accordingly, a white solid product was obtained (65.7 mg, yield of three steps: 20.4%). m.p. 195.2-197.7° C. $^1$H NMR (300 MHz, DMSO-d$_6$) δ 8.75 (d, J=1.3 Hz, 1H), 8.20 (s, 1H), 7.81-7.64 (m, 3H), 7.63-7.52 (m, 2H), 3.60 (s, 2H). EI-MS m/z: 321[M]$^+$.

Example 20

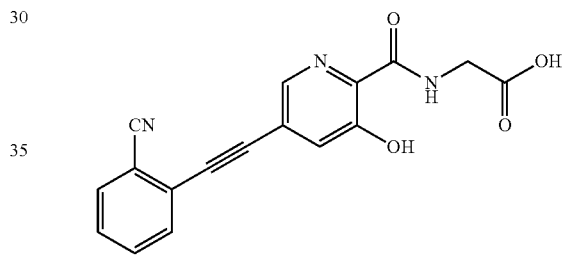

2-(3-Hydroxy-5-o-cyanophenylethynyl)picolinamido acetic acid

The preparation method is the same as that of Example 1, and propyne was replaced by o-cyanophenylacetylene (139.7 mg, 1.1 mmol). Accordingly, a white solid product was obtained (55.2 mg, yield of three steps: 17.2%). m.p. 182.2-184.8° C. $^1$H NMR (300 MHz, DMSO-d$_6$) δ 8.87 (d, J=1.3 Hz, 1H), 8.20 (s, 1H), 7.76 (dd, J=7.4, 2.1 Hz, 1H), 7.67-7.65 (m, 2H), 7.60-7.55 (m, 1H), 7.51-7.47 (m, 1H), 3.60 (s, 2H). EI-MS m/z: 321[M]$^+$.

Example 21

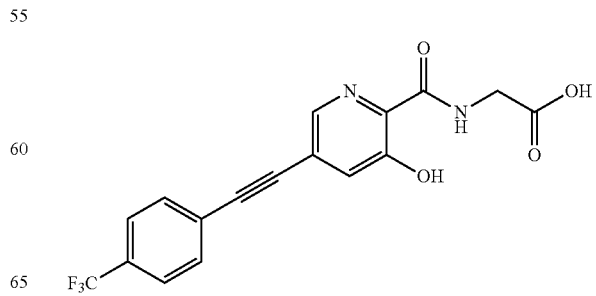

2-(3-Hydroxy-5-p-trifluoromethylphenylethynyl)picolinamido acetic acid

The preparation method is the same as that of Example 1, and propyne was replaced by p-trifluoromethylphenylacetylene (187.0 mg, 1.1 mmol). Accordingly, an ivory solid product was obtained (105.2 mg, yield of three steps: 28.8%). m.p. 201.5-2.3.8° C. $^1$H NMR (300 MHz, DMSO-$d_6$) δ 8.78 (d, J=1.2 Hz, 1H), 8.20 (s, 1H), 7.70 (d, J=1.2 Hz, 1H), 7.63-7.47 (m, 4H), 3.60 (s, 2H). EI-MS m/z: 364[M]$^+$.

Example 22

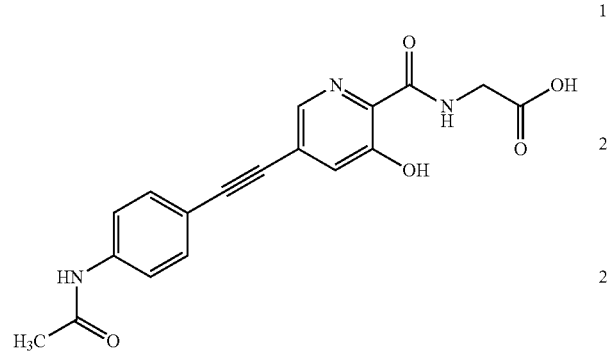

2-(3-Hydroxy-5-p-acetamidophenylethynyl)picolinamido acetic acid

The preparation method is the same as that of Example 1, and propyne was replaced by p-acetaminophenylacetylene (174.0 mg, 1.1 mmol). Accordingly, a white solid product was obtained (75.9 mg, yield of three steps: 21.5%). m.p. 251.2-253.7° C. $^1$H NMR (300 MHz, DMSO-$d_6$) δ 8.77 (d, J=1.3 Hz, 1H), 8.20 (s, 1H), 7.85-7.63 (m, 5H), 3.60 (s, 2H), 2.10 (s, 3H). EI-MS m/z: 353[M]$^+$.

Example 23

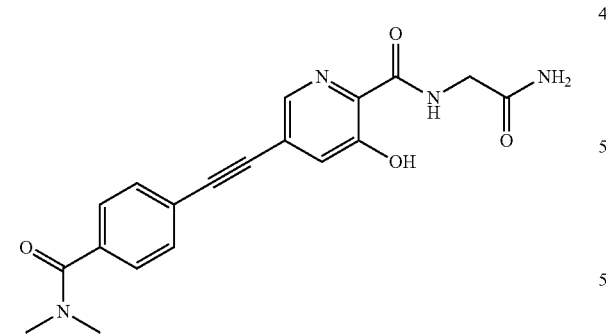

2-(3-Hydroxy-5-p-dimethylcarbamoylphenylethynyl)picolinamidoacetamide

The preparation method is the same as that of Example 1, propyne was replaced by p-dimethylcarbamoylphenylacetylene (190.3 mg, 1.1 mmol), and glycine methyl ester hydrochloride was replaced by glycinamide (110 mg, 1.5 mmol), accordingly, a white solid product was obtained (95.9 mg, yield of three steps: 26.2%). m.p. 229.1-231.5° C. $^1$H NMR (300 MHz, CDCl$_3$) δ 8.78 (d, J=1.3 Hz, 1H), 8.20 (s, 1H), 7.77-7.59 (m, 5H), 6.49 (s, 2H), 3.84 (s, 2H), 3.03 (s, 6H). EI-MS m/z: 366[M]$^+$.

Example 24

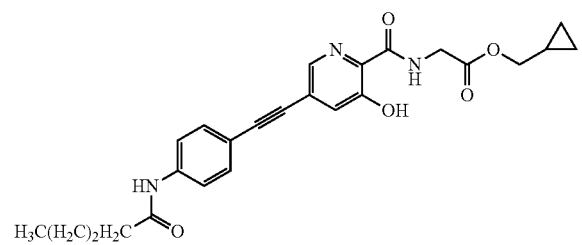

Cyclopropylmethyl 2-(3-hydroxy-5-p-pentanaminophenylethynyl)picolinamidoacetate

The preparation method is the same as that of Example 6, propyne was replaced by p-pentanamidophenylacetylene (205.7 mg, 1.1 mmol), and glycine methyl ester hydrochloride was replaced by cyclopropylmethyl glycinate, accordingly, a brown solid product was obtained (75.4 mg, yield of three steps: 12.3%). m.p. 178.5-180.2° C. $^1$H NMR (300 MHz, CDCl$_3$) δ 8.87 (d, J=1.2 Hz, 1H), 7.85-7.65 (m, 6H), 4.00 (d, J=7.0 Hz, 2H), 3.92 (s, 2H), 2.42 (t, J=8.0 Hz, 2H), 1.76-1.66 (m, 2H), 1.50-1.17 (m, 3H), 0.95 (t, J=7.9 Hz, 3H), 0.61-0.48 (m, 2H), 0.29-0.23 (m, 2H). EI-MS m/z: 449[M]$^+$.

Example 25

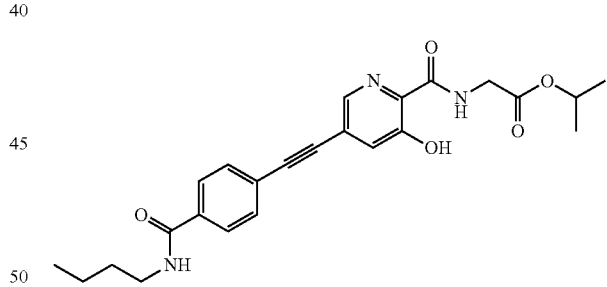

Isopropyl 2-(3-hydroxy-5-p-butylcarbamoylphenylethynyl)picolinamidoacetate

The preparation method is the same as that of Example 6, and propyne was replaced by p-butylcarbamoylphenylacetylene (205.7 mg, 1.1 mmol), and glycine methyl ester hydrochloride was replaced by isopropyl glycinate. Accordingly, a brown solid product was obtained (81.4 mg, yield of three steps: 18.6%). m.p. 187.2-189.5° C. $^1$H NMR (300 MHz, CDCl$_3$) δ 8.81 (s, 1H), 8.20 (s, 1H), 7.85-7.73 (m, 3H), 7.71-7.61 (m, 2H), 5.88 (s, 1H), 5.02-4.93 (m, 1H), 3.92 (s, 2H), 3.31 (t, J=7.5 Hz, 2H), 1.59-1.56 (m, J=7.8 Hz, 2H), 1.39-1.25 (m, 2H), 1.16 (d, J=6.8 Hz, 6H), 0.88 (t, J=7.9 Hz, 3H). EI-MS m/z: 437[M]$^+$.

Example 26

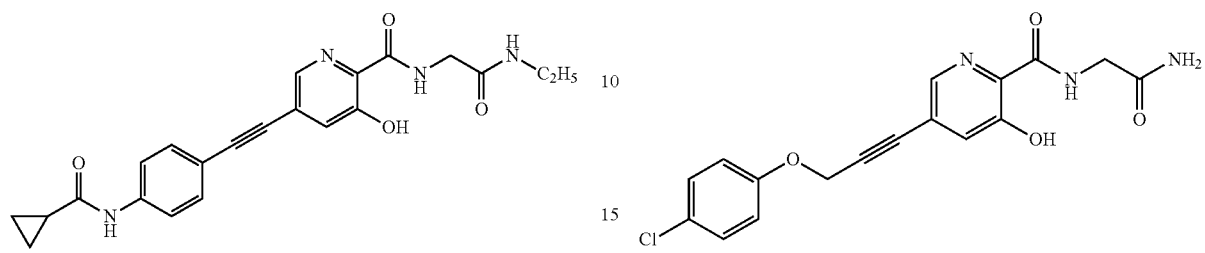

N-ethyl-(2-(3-hydroxy-5-p-cyclopropylcarboxamid-ophenylethynyl)picolinamido)acetamide The preparation method is the same as that of Example 6, and propyne was replaced by p-cyclopropylcarboxamid-ophenylacetylene (203.5 mg, 1.1 mmol), and glycine methyl ester hydrochloride was replaced by N-ethylglycinamide. Accordingly, a brown solid product was obtained (71.4 mg, yield of three steps: 18.3%). m.p. 195.2-197.7° C. $^1$H NMR (300 MHz, CDCl$_3$) (9.50 (s, 1H), 9.23 (s, 1H), 8.83 (d, J=1.3 Hz, 1H), 8.20 (s, 1H), 7.83-7.64 (m, 5H), 3.85 (s, 2H), 3.21 (q, J=6.3 Hz, 2H), 1.73-1.64 (m, 1H), 1.22 (t, J=6.3 Hz, 3H), 1.11-0.90 (m, 4H). EI-MS m/z: 406[M]$^+$.

Example 27

N-methyl-(2-(3-hydroxy-5-(3-phenoxypropyn-1-yl)picolinamido)acetamide

The preparation method is the same as that of Example 6, and propyne was replaced by 3-phenoxypropyne (145.2 mg, 1.1 mmol), and glycine methyl ester hydrochloride was replaced by N-methylglycinamide. Accordingly, a brown solid product was obtained (91.2 mg, yield of three steps: 26.9%). m.p. 192.2-194.4° C. $^1$H NMR (300 MHz, CDCl$_3$) δ 8.67 (d, J=1.2 Hz, 1H), 8.20 (s, 1H), 7.66 (d, J=1.2 Hz, 1H), 7.37-7.23 (m, 2H), 6.94-6.85 (m, 3H), 6.09 (s, 1H), 4.68 (s, 2H), 3.85 (s, 2H), 2.82 (s, 3H). EI-MS m/z: 339[M]$^+$.

Example 28

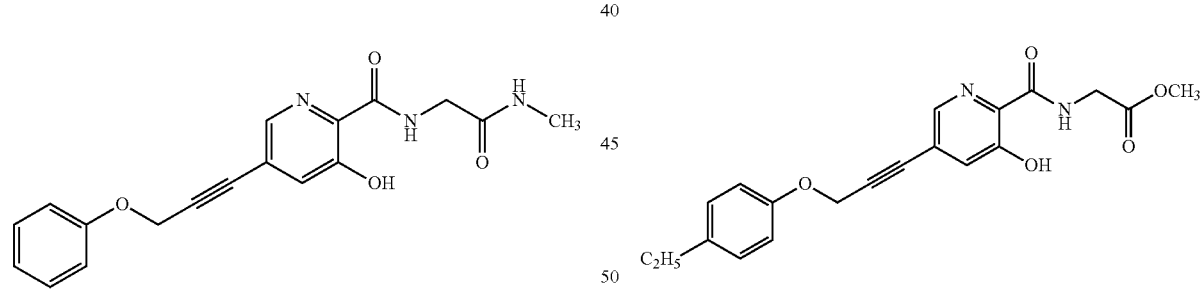

2-(3-Hydroxy-5-(3-p-chlorophenoxypropyn-1-yl)picolinamido acetamide

The preparation method is the same as that of Example 1, and propyne was replaced by 3-(p-chlorophenoxy)propyne (182.6 mg, 1.1 mmol), and glycine methyl ester hydrochloride was replaced by glycinamide. Accordingly, a brown product was obtained (54.0 mg, yield of three steps: 15.1%). m.p. 152.2-154.6° C. $^1$H NMR (300 MHz, DMSO-d$_6$) δ 8.91 (s, 1H), 8.64 (d, J=1.3 Hz, 1H), 7.68 (d, J=1.3 Hz, 1H), 7.36-7.26 (m, 2H), 7.12 (s, 2H), 6.99-6.89 (m, 2H), 4.73 (s, 2H), 3.85 (s, 2H). EI-MS m/z: 359[M]$^+$.

Example 29

Methyl 2-(3-hydroxy-5-(3-p-ethylphenoxypropyn-1-yl))picolinamido acetate

The preparation method is the same as that of Example 6, and propyne was replaced by 3-(p-ethylphenoxy)propyne (160.6 mg, 1.1 mmol). Accordingly, a white solid product was obtained (105.0 mg, yield: 28.5%). m.p. 112.2-114.3° C. $^1$H NMR (300 MHz, DMSO-d$_6$) δ 8.91 (s, 1H), 8.67 (d, J=1.3 Hz, 1H), 7.69 (d, J=1.3 Hz, 1H), 7.19-7.13 (m, 2H), 6.92-6.82 (m, 2H), 4.68 (s, 2H), 3.86 (s, 2H), 3.63 (s, 3H), 2.73-2.70 (m, J=6.6, 1.1 Hz, 2H), 1.19 (t, J=6.6 Hz, 3H). EI-MS m/z: 368[M]$^+$.

Example 30

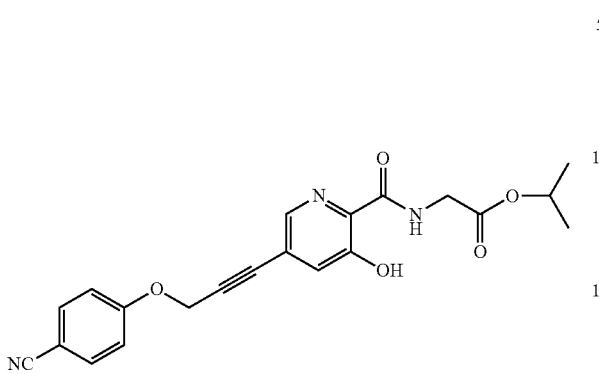

Isopropyl 2-(3-hydroxy-5-(3-p-cyanophenoxypropyn-1-yl))picolinamido acetate

The preparation method is the same as that of Example 6, and propyne was replaced by 3-(p-cyanophenoxy)propyne (172.7 mg, 1.1 mmol), and glycine methyl ester hydrochloride was replaced by isopropyl glycinate. Accordingly, a white solid product was obtained (126.0 mg, yield: 32.1%). m.p. 120.2-123.1° C. $^1$H NMR (300 MHz, DMSO-$d_6$) δ 8.91 (s, 1H), 8.62 (d, J=1.2 Hz, 1H), 7.79-7.66 (m, 3H), 7.20-7.09 (m, 2H), 4.91-4.87 (m, J=6.8 Hz, 1H), 4.68 (s, 2H), 3.86 (s, 2H), 1.14 (d, J=6.8 Hz, 6H). EI-MS m/z: 393[M]$^+$.

Example 31

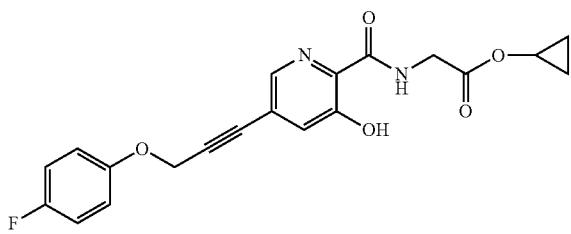 [SMILES: O=C(CNC(=O)c1ncc(C#CCOc2ccc(F)cc2)cc1O)OC1CC1]

Cyclopropyl 2-(3-hydroxy-5-(3-p-fluorophenoxy-propyn-1-yl))picolinamido acetate

The preparation method is the same as that of Example 6, and propyne was replaced by 3-(p-fluorophenoxy)propyne (165.0 mg, 1.1 mmol), and glycine methyl ester hydrochloride was replaced by glycine cyclopropyl ester. Accordingly, a white solid product was obtained (117.0 mg, yield: 30.4%). m.p. 107.2-109.9° C. $^1$H NMR (300 MHz, DMSO-$d_6$) 8.91 (s, 1H), 8.76 (d, J=1.3 Hz, 1H), 7.78 (d, J=1.3 Hz, 1H), 7.26-7.12 (m, 2H), 7.09-6.96 (m, 2H), 4.68 (s, 2H), 3.86 (s, 2H), 3.33 (p, J=7.0 Hz, 1H), 0.47-0.45 (m, 2H), 0.43-0.18 (m, 2H). EI-MS m/z: 384[M]$^+$.

Example 32

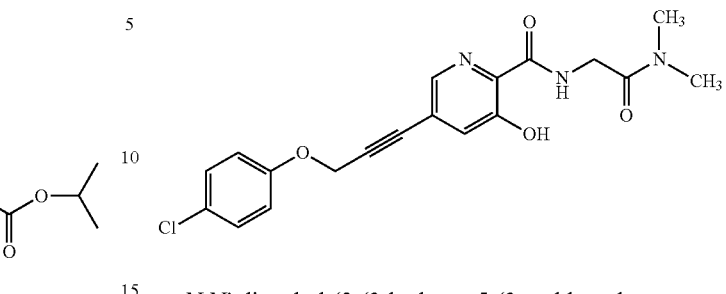

N,N'-dimethyl-(2-(3-hydroxy-5-(3-p-chlorophenoxy-propyn-1-yl))picolinamido)acetamide The preparation method is the same as that of Example 1, and propyne was replaced by 3-(p-chlorophenoxy)propyne (182.6 mg, 1.1 mmol), and glycine methyl ester hydrochloride was replaced by N,N'-dimethylglycinamide. Accordingly, a white solid product was obtained (97.0 mg, yield: 24.2%). m.p. 177.2-179.9° C. $^1$H NMR (300 MHz, DMSO-$d_6$) 8.91 (s, 1H), 8.67 (d, J=1.3 Hz, 1H), 7.68 (d, J=1.2 Hz, 1H), 7.36-7.26 (m, 2H), 7.00-6.89 (m, 2H), 4.68 (s, 2H), 3.85 (s, 2H), 2.87 (s, 6H). EI-MS m/z: 387[M]$^+$.

Example 33

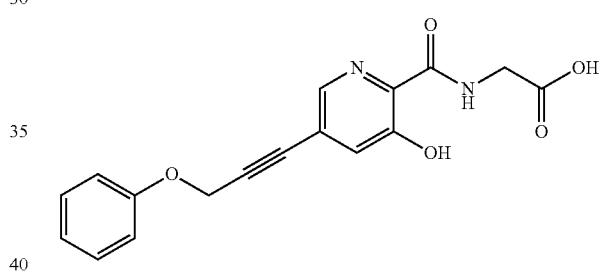

2-(3-Hydroxy-5-(3-phenoxypropyn-1-yl))picolinamido acetic acid

The preparation method is the same as that of Example 1, and propyne was replaced by 3-phenoxypropyne (145.2 mg, 1.1 mmol). Accordingly, a white solid product was obtained (77.1 mg, yield of two steps: 23.6%). m.p. 112.2-114.6° C. $^1$H NMR (300 MHz, DMSO-$d_6$) δ 8.69 (d, J=1.2 Hz, 1H), 8.20 (s, 1H), 7.65 (d, J=1.3 Hz, 1H), 7.37-7.23 (m, 2H), 6.94-6.85 (m, 3H), 4.68 (s, 2H), 3.60 (s, 2H). EI-MS m/z: 326[M]$^+$.

Example 34

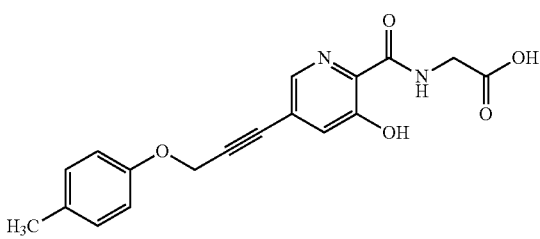 [SMILES: Cc1ccc(OCC#Cc2cnc(C(=O)NCC(=O)O)c(O)c2)cc1]

2-(3-Hydroxy-5-(3-p-tolyloxypropyn-1-yl))picolinamido acetic acid

The preparation method is the same as that of Example 1, and propyne was replaced by 3-(p-methylphenoxy)propyne (160.6 mg, 1.1 mmol). Accordingly, a white solid product was obtained (89.2 mg, yield of two steps: 24.7%). m.p. 162.2-164.3° C. $^1$H NMR (300 MHz, DMSO-d$_6$) δ 8.70 (d, J=1.3 Hz, 1H), 8.20 (s, 1H), 7.64 (d, J=1.2 Hz, 1H), 7.08-7.04 (m, 2H), 6.83-6.72 (m, 2H), 4.68 (s, 2H), 3.60 (s, 2H), 2.31 (s, 2H), 2.31 (d, J=2.2 Hz, 1H). EI-MS m/z: 340[M]$^+$.

Example 35

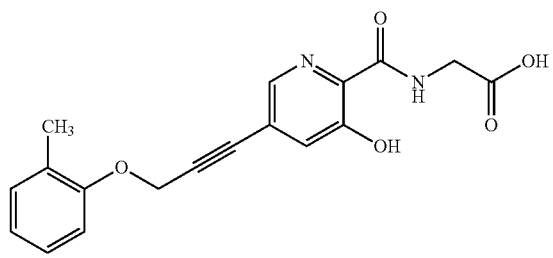

2-(3-Hydroxy-5-(3-o-methylphenoxypropyn-1-yl) picolinamido acetic acid

The preparation method is the same as that of Example 1, propyne was replaced by 3-(o-methylphenoxy)propyne (160.6 mg, 1.1 mmol). Accordingly, a white solid product was obtained (99.4 mg, yield of two steps: 29.1%). m.p. 154.3-156.7° C. $^1$H NMR (300 MHz, DMSO-d$_6$) δ 8.73 (d, J=1.3 Hz, 1H), 8.20 (s, 1H), 7.64 (d, J=1.3 Hz, 1H), 7.19-7.03 (m, 2H), 6.94-6.85 (m, 1H), 6.69-6.65 (m, 1H), 4.68 (s, 2H), 3.60 (s, 2H), 2.22 (d, J=1.0 Hz, 3H). EI-MS m/z: 340[M]$^+$.

Example 36

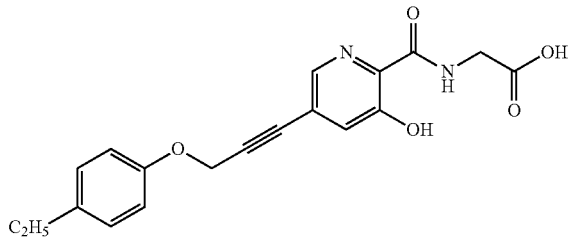 [SMILES: CCc1ccc(OCC#Cc2cnc(C(=O)NCC(=O)O)c(O)c2)cc1]

2-(3-Hydroxy-5-(3-p-ethylphenoxypropyn-1-yl)picolinamido acetic acid

The preparation method is the same as that of Example 1, and propyne was replaced by 3-(p-ethylphenoxy)propyne (176.0 mg, 1.1 mmol). Accordingly, a white solid product was obtained (110.3 mg, yield of two steps: 31.1%). m.p. 172.4-174.7° C. $^1$H NMR (300 MHz, DMSO-d$_6$) δ 8.69 (d, J=1.2 Hz, 1H), 8.20 (s, 1H), 7.65 (d, J=1.2 Hz, 1H), 7.14-7.10 (m, 2H), 6.85-6.75 (m, 2H), 4.68 (s, 2H), 3.60 (s, 2H), 2.73-2.69 (m, J=6.6, 1.1 Hz, 2H), 1.19 (t, J=6.6 Hz, 3H). EI-MS m/z: 354[M]$^+$.

Example 37

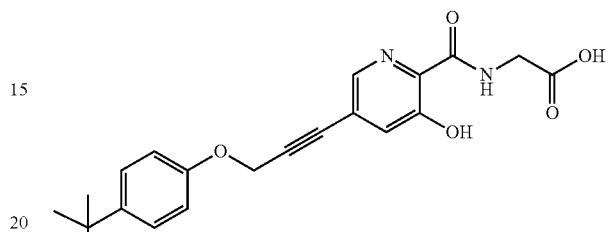

2-(3-Hydroxy-5-(3-p-tert-butylphenoxypropyn-1-yl)) picolinamido acetic acid

The preparation method is the same as that of Example 1, and propyne was replaced by 3-(p-tert-butylphenoxy)propyne (206.8 mg, 1.1 mmol). Accordingly, a white solid product was obtained (110.3 mg, yield of two steps: 31.1%). m.p. 180.1-182.5° C. $^1$H NMR (300 MHz, DMSO-d$_6$) δ 8.70 (d, J=1.3 Hz, 1H), 8.20 (s, 1H), 7.64 (d, J=1.2 Hz, 1H), 7.37-7.26 (m, 2H), 6.82-6.72 (m, 2H), 4.68 (s, 2H), 3.60 (s, 2H), 1.28 (s, 9H). EI-MS m/z: 382[M]$^+$.

Example 38

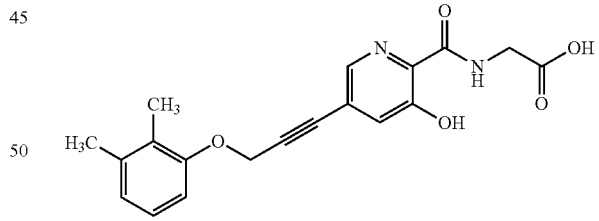

2-(3-Hydroxy-5-(3-(2,3-dimethylphenyl)oxypropyn-1-yl))picolinamido acetic acid The preparation method is the same as that of Example 1, and propyne was replaced by 3-(2,3-dimethylphenyl)oxypropyne (176.0 mg, 1.1 mmol). Accordingly, a white solid product was obtained (60.3 mg, yield of two steps: 16.9%). m.p. 182.2-184.3° C. $^1$H NMR (300 MHz, DMSO-d$_6$) δ 8.69 (d, J=1.3 Hz, 1H), 8.20 (s, 1H), 7.65 (d, J=1.2 Hz, 1H), 7.06 (t, J=7.5 Hz, 1H), 6.76-6.63 (m, 2H), 4.68 (s, 2H), 3.60 (s, 2H), 2.25-2.13 (m, 6H). EI-MS m/z: 354[M]$^+$.

Example 39

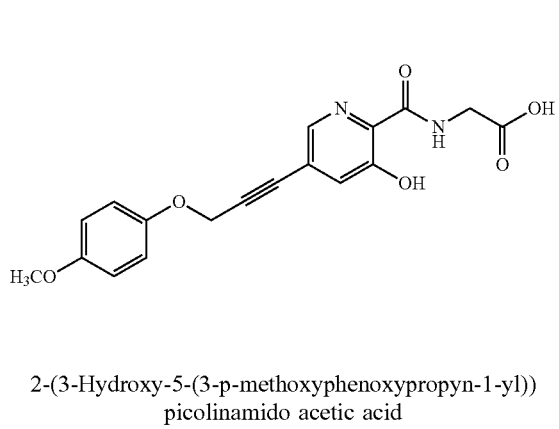

2-(3-Hydroxy-5-(3-p-methoxyphenoxypropyn-1-yl))picolinamido acetic acid

The preparation method is the same as that of Example 1, and propyne was replaced by 3-p-methoxyphenoxypropyne (180.0 mg, 1.1 mmol). Accordingly, a white solid product was obtained (80.1 mg, yield of two steps: 22.4%). m.p. 223.3-225.6° C. $^1$H NMR (300 MHz, DMSO-$d_6$) δ 8.73 (d, J=1.3 Hz, 1H), 8.20 (s, 1H), 7.65 (d, J=1.2 Hz, 1H), 6.79 (s, 4H), 4.68 (s, 2H), 3.80 (s, 3H), 3.60 (s, 2H). EI-MS m/z: 356[M]$^+$.

Example 40

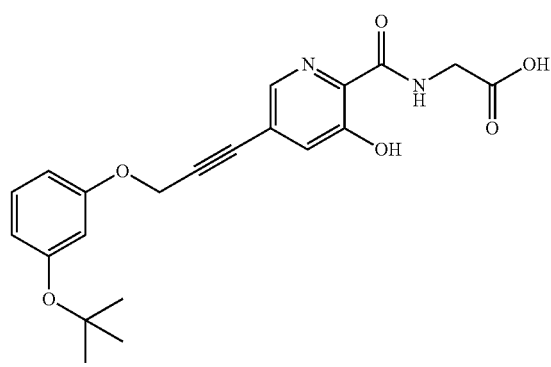 [SMILES: CC(C)(C)Oc1cccc(OCC#Cc2cnc(C(=O)NCC(=O)O)c(O)c2)c1]

2-(3-Hydroxy-5-(3-m-tert-butoxyphenoxypropyn-1-yl))picolinamido acetic acid

The preparation method is the same as that of Example 1, and propyne was replaced by 3-m-tert-butoxyphenoxypropyne (224.4 mg, 1.1 mmol). Accordingly, a white solid product was obtained (85.5 mg, yield of two steps: 21.5%). m.p. 237.2-239.4° C. $^1$H NMR (300 MHz, DMSO-$d_6$) δ 8.68 (d, J=1.2 Hz, 1H), 8.20 (s, 1H), 7.62 (d, J=1.2 Hz, 1H), 7.24 (t, J=7.5 Hz, 1H), 6.69-6.67 (m, J=5.7, 1.9 Hz, 2H), 6.48 (t, J=2.0 Hz, 1H), 4.68 (s, 2H), 3.60 (s, 2H), 1.41 (s, 9H). EI-MS m/z: 398[M]$^+$.

Example 41

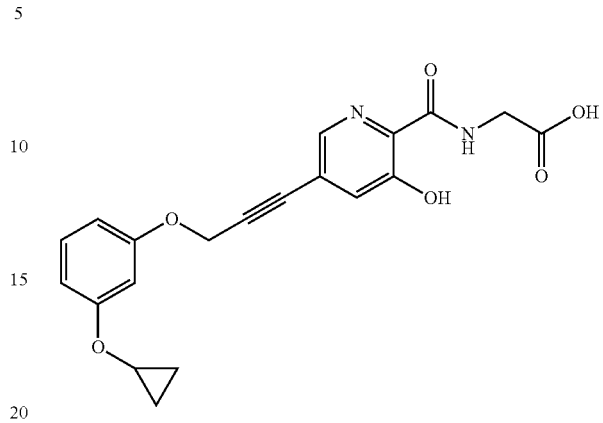

2-(3-Hydroxy-5-(3-m-cyclopropoxyphenoxypropyn-1-yl))picolinamido acetic acid

The preparation method is the same as that of Example 1, and propyne was replaced by 3-m-cyclopropoxyphenoxypropyne (206.8 mg, 1.1 mmol). Accordingly, a white solid product was obtained (95.0 mg, yield of two steps: 24.9%). m.p. 212.3-214.7° C. $^1$H NMR (300 MHz, DMSO-$d_6$) δ 8.80 (d, J=1.3 Hz, 1H), 8.20 (s, 1H), 7.78 (d, J=1.2 Hz, 1H), 7.25 (t, J=7.5 Hz, 1H), 6.69-6.67 (m, 2H), 6.48 (t, J=2.1 Hz, 1H), 4.68 (s, 2H), 3.60 (s, 2H), 3.17-3.14 (m, 1H), 0.74-0.57 (m, 2H), 0.52-0.32 (m, 2H). EI-MS m/z: 382[M]$^+$.

Example 42

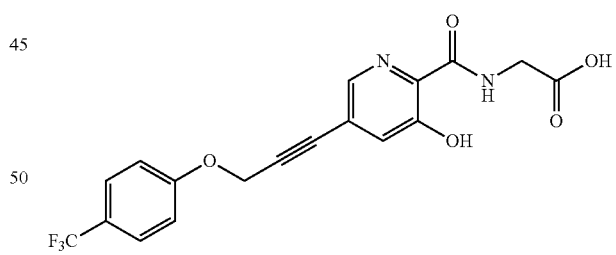

2-(3-Hydroxy-5-(3-p-trifluoromethylphenoxypropyn-1-yl))picolinamido acetic acid

The preparation method is the same as that of Example 1, and propyne was replaced by 3-p-trifluoromethylphenoxypropyne (220.0 mg, 1.1 mmol). Accordingly, a white solid product was obtained (79.0 mg, yield of two steps: 20.3%). m.p. 197.2-199.5° C. $^1$H NMR (300 MHz, DMSO-$d_6$) δ 8.70 (d, J=1.2 Hz, 1H), 8.20 (s, 1H), 7.66 (d, J=1.2 Hz, 1H), 7.56-7.47 (m, 2H), 6.92-6.82 (m, 2H), 4.68 (s, 2H), 3.60 (s, 2H). EI-MS m/z: 394 [M]$^+$.

Example 43

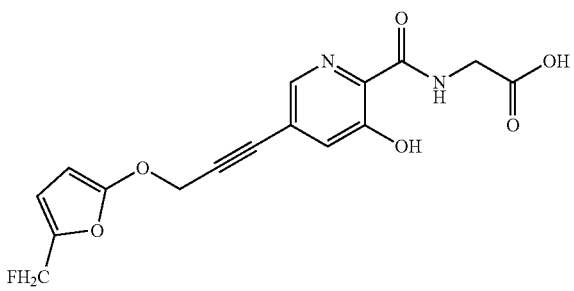

2-(3-Hydroxy-5-3-(5-fluoromethylfuran-2-yloxy)-1-propynyl)picolinamido acetic acid The preparation method is the same as that of Example 1, and propyne was replaced by 3-(5-fluoromethylfuran-2-yloxy)propyne (180.0 mg, 1.1 mmol). Accordingly, a white solid product was obtained (95.0 mg, yield of two steps: 26.5%). m.p. 187.2-189.3° C. $^1$H NMR (300 MHz, DMSO-$d_6$) δ 8.71 (d, J=1.2 Hz, 1H), 8.20 (s, 1H), 7.63 (d, J=1.2 Hz, 1H), 7.35-7.31 (m, 1H), 6.90-6.79 (m, 1H), 5.43 (t, J=1.1 Hz, 1H), 5.27 (t, J=1.1 Hz, 1H), 4.68 (s, 2H), 3.60 (s, 2H). EI-MS m/z: 348 [M]$^+$.

Example 44

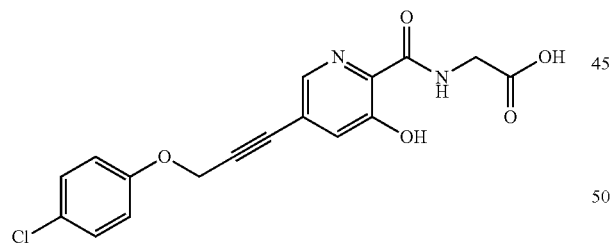

2-(3-Hydroxy-5-(3-p-chlorophenoxypropyn-1-yl))picolinamido acetic acid

The preparation method is the same as that of Example 1, and propyne was replaced by 3-p-chlorophenoxypropyne (182.6 mg, 1.1 mmol). Accordingly, a white solid product was obtained (95.0 mg, yield of two steps: 26.5%). m.p. 132.7-134.7° C. $^1$H NMR (300 MHz, DMSO-$d_6$) δ 8.69 (d, J=1.2 Hz, 1H), 8.20 (s, 1H), 7.65 (d, J=1.3 Hz, 1H), 7.33-7.22 (m, 2H), 6.84-6.73 (m, 2H), 4.80 (s, 2H), 3.88 (s, 2H). EI-MS m/z: 360 [M]$^+$.

Example 45

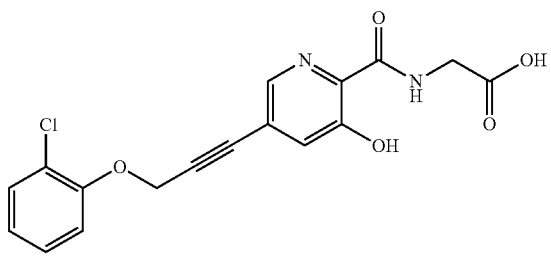 [SMILES: O=C(O)CNC(=O)c1ncc(C#CCOc2ccccc2Cl)cc1O]

2-(3-Hydroxy-5-(3-o-chlorophenoxypropyn-1-yl))picolinamido acetic acid

The preparation method is the same as that of Example 1, and propyne was replaced by 3-o-chlorophenoxypropyne (182.6 mg, 1.1 mmol). Accordingly, a white solid product was obtained (84.0 mg, yield of two steps: 23.6%). m.p. 127.1-129.4° C. $^1$H NMR (300 MHz, DMSO-$d_6$) δ 8.74 (d, J=1.2 Hz, 1H), 8.20 (s, 1H), 7.64 (d, J=1.3 Hz, 1H), 7.31 (dd, J=7.5, 2.0 Hz, 1H), 7.16-7.10 (m, 1H), 6.98-6.92 (m, 1H), 6.83 (dd, J=7.5, 2.1 Hz, 1H), 4.68 (s, 2H), 3.60 (s, 2H). EI-MS m/z: 360 [M]$^+$.

Example 46

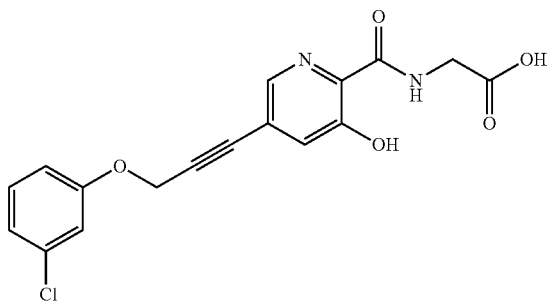 [SMILES: O=C(O)CNC(=O)c1ncc(C#CCOc2cccc(Cl)c2)cc1O]

2-(3-Hydroxy-5-(3-m-chlorophenoxypropyn-1-yl))picolinamido acetic acid

The preparation method is the same as that of Example 1, and propyne was replaced by 3-m-chlorophenoxypropyne (182.6 mg, 1.1 mmol). Accordingly, a white solid product was obtained (74.0 mg, yield of two steps: 20.5%). m.p. 110.2-112.6° C. $^1$H NMR (300 MHz, DMSO-$d_6$) δ 8.69 (d, J=1.2 Hz, 1H), 8.20 (s, 1H), 7.64 (d, J=1.2 Hz, 1H), 7.24 (t, J=7.5 Hz, 1H), 7.09-7.05 (m, 1H), 6.94-6.76 (m, 2H), 4.68 (s, 2H), 3.60 (s, 2H). EI-MS m/z: 360 [M]$^+$.

Example 47

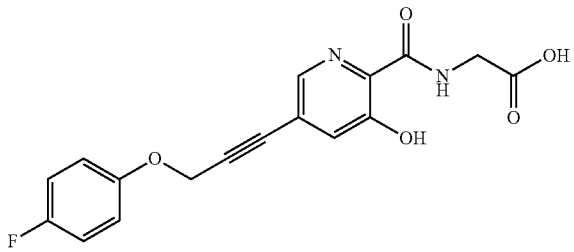 [SMILES: O=C(O)CNC(=O)c1ncc(C#CCOc2ccc(F)cc2)cc1O]

2-(3-Hydroxy-5-(3-p-fluorophenoxypropyn-1-yl))
picolinamido acetic acid

The preparation method is the same as that of Example 1, and propyne was replaced by 3-p-fluorophenoxypropyne (165.0 mg, 1.1 mmol). Accordingly, a white solid product was obtained (88.0 mg, yield of two steps: 25.5%). m.p. 171.2-173.7° C. $^1$H NMR (300 MHz, DMSO-d$_6$) δ 8.70 (d, J=1.2 Hz, 1H), 8.20 (s, 1H), 7.64 (d, J=1.3 Hz, 1H), 7.09-6.96 (m, 2H), 6.88-6.75 (m, 2H), 4.68 (s, 2H), 3.60 (s, 2H). EI-MS m/z: 344 [M]$^+$.

Example 48

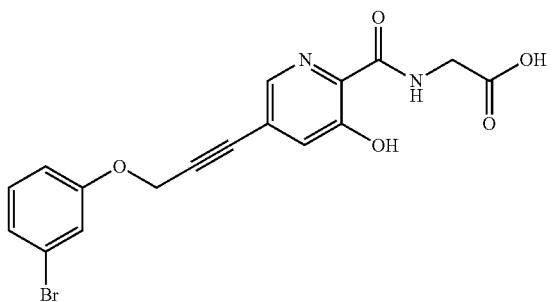 [SMILES: O=C(O)CNC(=O)c1ncc(C#CCOc2cccc(Br)c2)cc1O]

2-(3-Hydroxy-5-(3-m-bromophenoxypropyn-1-yl))
picolinamido acetic acid

The preparation method is the same as that of Example 1, and propyne was replaced by 3-m-bromophenoxypropyne (165.0 mg, 1.1 mmol). Accordingly, a white solid product was obtained (88.0 mg, yield of two steps: 25.5%). m.p. 132.1-134.5° C. $^1$H NMR (300 MHz, DMSO-d$_6$) δ 8.69 (d, J=1.2 Hz, 1H), 8.20 (s, 1H), 7.64 (d, J=1.3 Hz, 1H), 7.37-7.33 (m, 1H), 7.15 (t, J=7.5 Hz, 1H), 7.01-6.84 (m, 2H), 4.68 (s, 2H), 3.60 (s, 2H). EI-MS m/z: 404 [M]$^+$.

Example 49

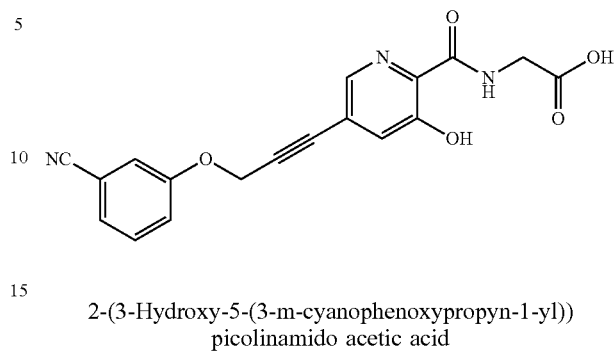

2-(3-Hydroxy-5-(3-m-cyanophenoxypropyn-1-yl))
picolinamido acetic acid

The preparation method is the same as that of Example 1, and propyne was replaced by 3-m-cyanophenoxypropyne (127.7 mg, 1.1 mmol). Accordingly, a white solid product was obtained (68.0 mg, yield of two steps: 19.4%). m.p. 181.2-183.4° C. $^1$H NMR (300 MHz, DMSO-d$_6$) δ 8.69 (d, J=1.3 Hz, 1H), 8.20 (s, 1H), 7.75-7.61 (m, 3H), 7.19-7.09 (m, 2H), 4.68 (s, 2H), 3.60 (s, 2H). EI-MS m/z: 351 [M]$^+$.

Example 50

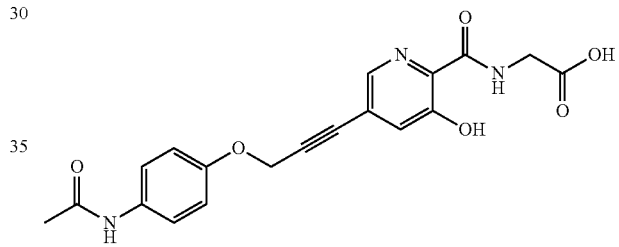

2-(3-Hydroxy-5-(3-p-acetamidophenoxypropyn-1-yl))picolinamido acetic acid

The preparation method is the same as that of Example 1, and propyne was replaced by 3-p-acetamidophenoxypropyne (207.9 mg, 1.1 mmol). Accordingly, a yellow solid product was obtained (77.0 mg, yield of two steps: 20.1%). m.p. 117.1-119.3° C. $^1$H NMR (300 MHz, DMSO-d$_6$) δ 8.69 (d, J=1.3 Hz, 1H), 8.20 (s, 1H), 7.65 (d, J=1.2 Hz, 1H), 7.57 (s, 1H), 7.48-7.37 (m, 2H), 6.88-6.78 (m, 2H), 4.68 (s, 2H), 3.60 (s, 2H), 2.10 (s, 3H). EI-MS m/z: 383 [M]$^+$.

Example 51

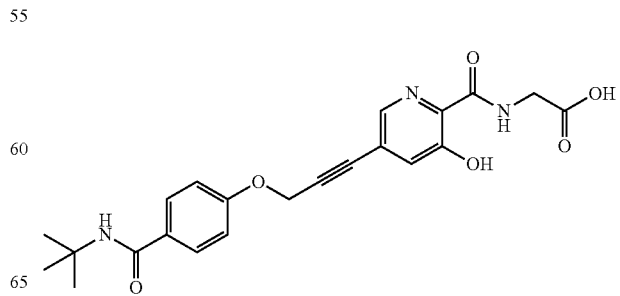

2-(3-Hydroxy-5-(3-p-tert-butylcarbamoylphenoxy-propyn-1-yl))picolinamido acetic acid The preparation method is the same as that of Example 1, and propyne was replaced by 3-(p-tert-butylcarbamoylphenoxy)propyne (254.1 mg, 1.1 mmol). Accordingly, a brown solid product was obtained (77.0 mg, yield of two steps: 20.1%). m.p. 141.2-143.5° C. $^1$H NMR (300 MHz, DMSO-$d_6$) δ 8.73 (d, J=1.3 Hz, 1H), 8.20 (s, 1H), 7.73-7.62 (m, 3H), 6.97-6.86 (m, 2H), 5.99 (s, 1H), 4.68 (s, 2H), 3.60 (s, 2H), 1.47 (s, 9H). EI-MS m/z: 425 [M]$^+$.

Example 52

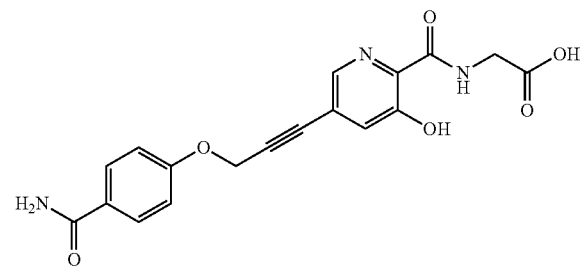 [SMILES: NC(=O)c1ccc(OCC#Cc2cnc(C(=O)NCC(=O)O)c(O)c2)cc1]

2-(3-Hydroxy-5-(3-p-carbamoylphenoxypropyn-1-yl))picolinamido acetic acid

The preparation method is the same as that of Example 1, and propyne was replaced by 3-p-carbamoylphenoxypropyne (190.3 mg, 1.1 mmol). Accordingly, a brown solid product was obtained (76.0 mg, yield of two steps: 20.6%). m.p. 122.1-124.7° C. $^1$H NMR (300 MHz, DMSO-$d_6$) δ 8.69 (d, J=1.2 Hz, 1H), 8.20 (s, 1H), 7.69-7.56 (m, 3H), 6.97-6.86 (m, 2H), 6.15 (s, 2H), 4.68 (s, 2H), 3.60 (s, 2H). EI-MS m/z: 369 [M]$^+$.

Example 53

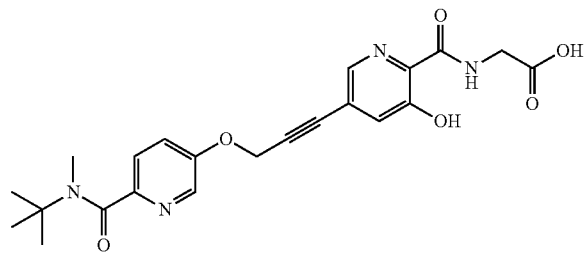 [SMILES: CN(C(=O)c1ccc(OCC#Cc2cnc(C(=O)NCC(=O)O)c(O)c2)cn1)C(C)(C)C]

2-(3-Hydroxy-5-(3-(N-methyl-N-tert-butylcarbamoyl)pyridin-3-yloxy)propyn-1-yl)picolinamido acetic acid The preparation method is the same as that of Example 1, and propyne was replaced by 3-((N-methyl-N-tert-butylcarbamoyl)pyridin-3-yloxy)propyne (269.5 mg, 1.1 mmol). Accordingly, a white solid product was obtained (106.0 mg, yield of two steps: 24.1%). m.p. 137.1-139.3° C. $^1$H NMR (300 MHz, DMSO-$d_6$) δ 8.70 (d, J=1.2 Hz, 1H), 8.20 (s, 1H), 7.63-7.52 (m, 2H), 7.06-6.95 (m, 2H), 4.68 (s, 2H), 3.60 (s, 2H), 2.99 (s, 3H), 1.21 (s, 9H). EI-MS m/z: 440 [M]$^+$.

Example 54

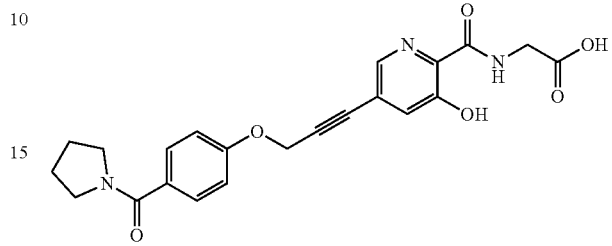

2-(3-Hydroxy-5-(3-(4-(pyrrolidin-1-carbonyl)phenoxy)propyn-1-yl))picolinamido acetic acid The preparation method is the same as that of Example 1, and propyne was replaced by 3-((4-(pyrrolidin-1-carbonyl)phenoxy))propyne (251.9 mg, 1.1 mmol). Accordingly, a white solid product was obtained (56.0 mg, yield of two steps: 13.2%). m.p. 154.1-156.8° C. $^1$H NMR (300 MHz, DMSO-$d_6$) δ 8.70 (d, J=1.3 Hz, 1H), 8.20 (s, 1H), 7.64 (d, J=1.2 Hz, 1H), 7.55-7.44 (m, 2H), 6.95-6.84 (m, 2H), 4.68 (s, 2H), 3.60 (s, 2H), 3.56-3.42 (m, 4H), 2.03-1.87 (m, 4H). EI-MS m/z: 423 [M]$^+$.

Example 55

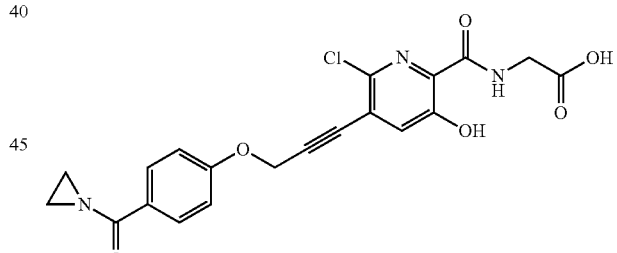

2-(3-Hydroxy-5-(3-((4-(aziridinyl-1-carbonyl))phenoxypropyn-1-yl)-6-chloro)picolinamido acetic acid The preparation method is the same as that of Example 1, and 3-hydroxy-5-bromopyridine-2-carboxylic acid was replaced by 3-hydroxy-5-bromo-6-chloropyridine-2-carboxylic acid, and propyne was replaced by 3-((4-(aziridinyl-1-carbonyl))phenoxy)propyne (251.9 mg, 1.1 mmol). Accordingly, a white solid product was obtained (76.0 mg, yield of three steps: 17.7%). m.p. 147.2-149.2° C. $^1$H NMR (300 MHz, DMSO-$d_6$) δ 8.20 (s, 1H), 7.92-7.77 (m, 3H), 7.23-7.12 (m, 2H), 4.68 (s, 2H), 3.60 (s, 2H), 1.61 (s, 4H). EI-MS m/z: 429 [M]$^+$.

Example 56

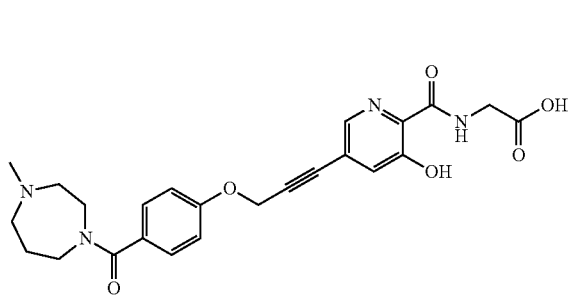 [SMILES: CN1CCCN(C(=O)c2ccc(OCC#Cc3cnc(C(=O)NCC(=O)O)c(O)c3)cc2)CC1]

2-(3-Hydroxy-5-(3-(4-(4-methyl-1,4-diazepan-1-carbonyl)phenoxy)propyn-1-yl)picolinamido acetic acid The preparation method is the same as that of Example 1, and propyne was replaced by 3-((4-(4-methyl-1,4-diazepan-1-carbonyl)phenoxy))propyne (299.2 mg, 1.1 mmol). Accordingly, a white solid product was obtained (86.0 mg, yield of two steps: 18.4%). m.p. 168.9-172.1° C. $^1$H NMR (300 MHz, DMSO-d$_6$) δ 8.73 (d, J=1.2 Hz, 1H), 8.20 (s, 1H), 7.66 (d, J=1.3 Hz, 1H), 7.55-7.45 (m, 2H), 6.95-6.85 (m, 2H), 4.68 (s, 2H), 3.60 (s, 2H), 3.60-3.27 (m, 4H), 2.90 (t, J=5.9 Hz, 2H), 2.66 (t, J=6.4 Hz, 2H), 2.27 (s, 3H), 1.73-1.65 (m, 2H). EI-MS m/z: 466 [M]$^+$.

Example 57

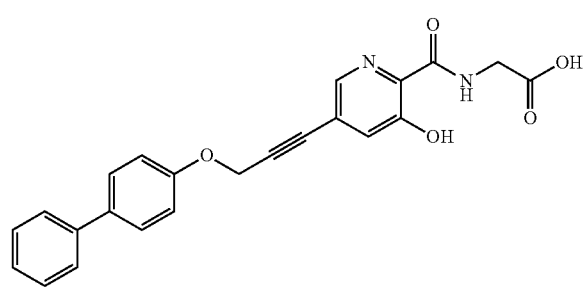 [SMILES: O=C(O)CNC(=O)c1ncc(C#CCOc2ccc(-c3ccccc3)cc2)cc1O]

2-(3-Hydroxy-5-(3-p-phenylphenoxypropyn-1-yl))picolinamido acetic acid

The preparation method is the same as that of Example 1, and propyne was replaced by 3-p-phenylphenoxypropyne (228.8 mg, 1.1 mmol). Accordingly, a white solid product was obtained (95.0 mg, yield of two steps: 23.6%). m.p. 201.5-203.7° C. $^1$H NMR (300 MHz, DMSO-d$_6$) δ 8.69 (d, J=1.3 Hz, 1H), 8.20 (s, 1H), 7.73 (d, J=1.3 Hz, 1H), 7.64-7.53 (m, 2H), 7.55-7.38 (m, 4H), 7.36-7.30 (m, 1H), 7.12-7.01 (m, 2H), 4.68 (s, 2H), 3.60 (s, 2H). EI-MS m/z: 402 [M]$^+$.

Example 58

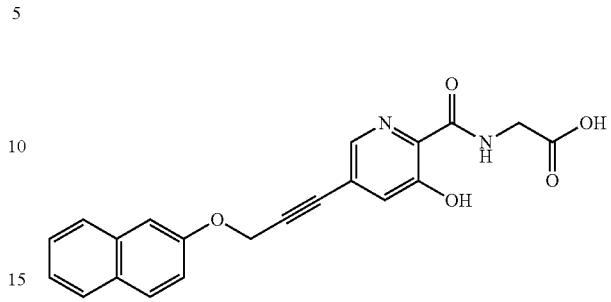

2-(3-Hydroxy-5-(3-(naphthalen-2-oxy)propyn-1-yl))picolinamido acetic acid

The preparation method is the same as that of Example 1, and propyne was replaced by 3-(naphthalen-2-oxy)propyne (200.2 mg, 1.1 mmol). Accordingly, a white solid product was obtained (45.0 mg, yield of two steps: 11.9%). m.p. 211.5-213.7° C. $^1$H NMR (300 MHz, DMSO-d$_6$) δ 8.80 (d, J=1.2 Hz, 1H), 8.20 (s, 1H), 7.76 (d, J=1.3 Hz, 1H), 7.72-7.62 (m, 2H), 7.56 (dt, J=7.3, 1.6 Hz, 1H), 7.41-7.36 (m, 2H), 7.14 (dd, J=7.9, 1.5 Hz, 1H), 6.97 (t, J=1.7 Hz, 1H), 4.91 (s, 2H), 3.89 (s, 2H). EI-MS m/z: 376 [M]$^+$.

Example 59

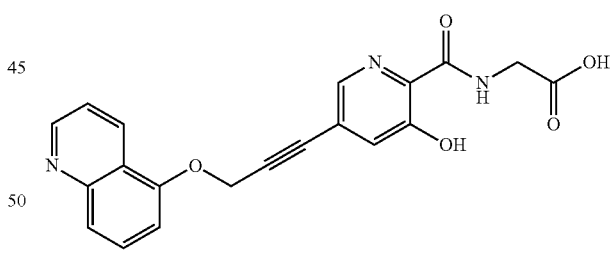

2-(3-Hydroxy-5-(3-(quinolin-5-oxy)propyn-1-yl))picolinamido acetic acid

The preparation method is the same as that of Example 1, and propyne was replaced by 3-(quinolin-5-oxy)propyne (201.3 mg, 1.1 mmol). Accordingly, a brown solid product was obtained (65.0 mg, yield of two steps: 17.2%). m.p. 223.1-225.6° C. $^1$H NMR (300 MHz, DMSO-d$_6$) δ 8.83-8.71 (m, 2H), 8.44 (dd, J=7.4, 1.5 Hz, 1H), 8.20 (s, 1H), 7.80-7.67 (m, 2H), 7.53-7.49 (m, 2H), 6.70-6.68 (m, 1H), 4.68 (s, 2H), 3.60 (s, 2H). EI-MS m/z: 377 [M]$^+$.

Example 60

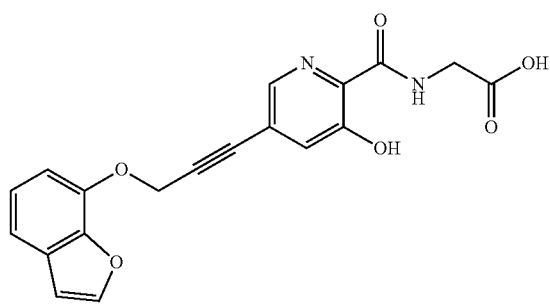 [SMILES: O=C(O)CNC(=O)c1ncc(C#CCOc2cccc3ccoc23)cc1O]

2-(3-Hydroxy-5-(3-(benzofuran-7-oxy)propyn-1-yl))picolinamido acetic acid

The preparation method is the same as that of Example 1, and propyne was replaced by 3-(benzofuran-7-oxy)propyne (201.3 mg, 1.1 mmol). Accordingly, a brown solid product was obtained (75.0 mg, yield of two steps: 20.4%). m.p. 196.1-198.7° C. $^1$H NMR (300 MHz, DMSO-d$_6$) δ 8.70 (d, J=1.2 Hz, 1H), 8.20 (s, 1H), 7.66 (d, J=1.3 Hz, 1H), 7.52 (d, J=7.5 Hz, 1H), 7.23-7.06 (m, 2H), 6.99 (dd, J=7.3, 1.8 Hz, 1H), 6.72 (dd, J=7.5, 1.5 Hz, 1H), 4.68 (s, 2H), 3.60 (s, 2H). EI-MS m/z: 366 [M]$^+$.

Example 61

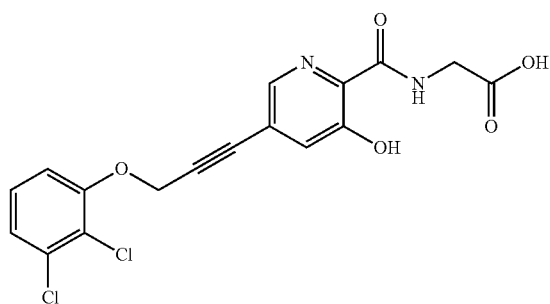 [SMILES: O=C(O)CNC(=O)c1ncc(C#CCOc2cccc(Cl)c2Cl)cc1O]

2-(3-Hydroxy-5-(3-(2,3-dichlorophenyl)oxypropyn-1-yl))picolinamido acetic acid

The preparation method is the same as that of Example 1, and propyne was replaced by 3-(2,3-dichlorophenyl)oxypropyne (218.9 mg, 1.1 mmol). Accordingly, a white solid product was obtained (62.0 mg, yield of two steps: 15.7%). m.p. 152.2-154.6° C. $^1$H NMR (300 MHz, DMSO-d$_6$) δ 8.74 (d, J=1.3 Hz, 1H), 8.20 (s, 1H), 7.64 (d, J=1.3 Hz, 1H), 7.28 (dd, J=7.5, 2.1 Hz, 1H), 7.17 (t, J=7.5 Hz, 1H), 6.71 (dd, J=7.4, 2.0 Hz, 1H), 4.68 (s, 2H), 3.60 (s, 2H). EI-MS m/z: 394 [M]$^+$.

Example 62

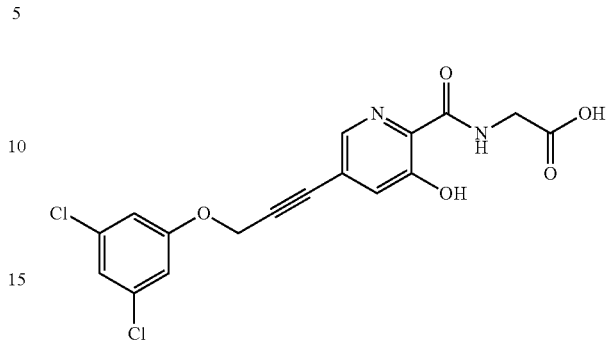

2-(3-Hydroxy-5-(3-(3,5-dichlorophenyl)oxypropyn-1-yl))picolinamido acetic acid

The preparation method is the same as that of Example 1, and propyne was replaced by 3-(3,5-dichlorophenyl)oxypropyne (218.9 mg, 1.1 mmol). Accordingly, a white solid product was obtained (74.0 mg, yield of two steps: 18.7%). m.p. 157.5-159.4° C. $^1$H NMR (300 MHz, DMSO-d$_6$) δ 8.68 (d, J=1.2 Hz, 1H), 8.20 (s, 1H), 7.66 (d, J=1.2 Hz, 1H), 7.42 (d, J=2.0 Hz, 1H), 7.26 (dd, J=7.5, 2.0 Hz, 1H), 6.97 (d, J=7.5 Hz, 1H), 4.68 (s, 2H), 3.60 (s, 2H). EI-MS m/z: 394 [M]$^+$.

Example 63

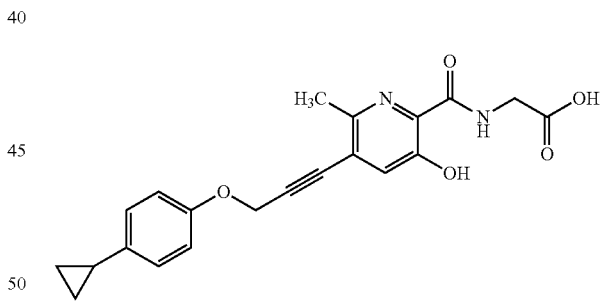

2-(3-Hydroxy-5-(3-p-cyclopropylphenoxypropyn-1-yl)-6-methyl)picolinamido acetic acid In accordance with the method of Example 1, 3-hydroxy-5-bromopicolinic acid was replaced by 3-hydroxy-5-bromo-6-methylpicolinic acid (372 mg, 2 mmol), and propyne was replaced by 3-p-cyclopropylphenoxypropyne (189.2 mg, 1.1 mmol). Accordingly, a light yellow solid product was obtained (82 mg, yield: 21.5%). m.p. 177.5-179.4° C. 1H NMR (300 MHz, DMSO-d6) δ 8.91 (s, 1H), 7.77 (s, 1H), 7.17-7.06 (m, 2H), 6.93-6.82 (m, 2H), 4.68 (s, 2H), 3.60 (s, 2H), 2.76 (s, 3H), 1.18-1.03 (m, 2H), 0.90-0.72 (m, 2H). EI-MS m/z: 380 [M]$^+$.

Example 64

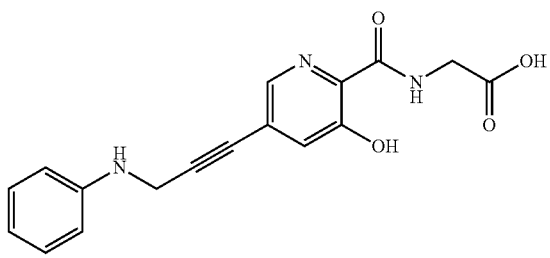 [SMILES: O=C(O)CNC(=O)c1ncc(C#CCNc2ccccc2)cc1O]

2-(3-Hydroxy-5-(3-anilinopropyn-1-yl))picolinamido acetic acid

The preparation method is the same as that of Example 1, and propyne was replaced by 3-anilinopropyne (144.1 mg, 1.1 mmol). Accordingly, a white solid product was obtained (64.0 mg, yield of two steps: 20.0%). m.p. 131.1-133.5° C. $^1$H NMR (300 MHz, DMSO-$d_6$) δ 8.75 (d, J=1.3 Hz, 1H), 8.20 (s, 1H), 7.63 (d, J=1.2 Hz, 1H), 7.11-6.97 (m, 2H), 6.74-6.69 (m, 1H), 6.64-6.52 (m, 2H), 4.29 (s, 1H), 3.80 (s, 2H), 3.60 (s, 2H). EI-MS m/z: 325 [M]$^+$.

Example 65

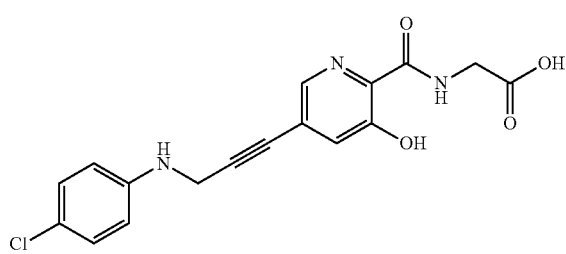 [SMILES: O=C(O)CNC(=O)c1ncc(C#CCNc2ccc(Cl)cc2)cc1O]

2-(3-Hydroxy-5-((3-p-chloroanilinopropyn-1-yl))picolinamido acetic acid

The preparation method is the same as that of Example 1, and propyne was replaced by 3-p-chloroanilinopropyne (181.1 mg, 1.1 mmol). Accordingly, a white solid product was obtained (78.0 mg, yield of two steps: 21.7%). m.p. 137.2-139.3° C. $^1$H NMR (300 MHz, DMSO-$d_6$) δ 8.73 (d, J=1.3 Hz, 1H), 8.20 (s, 1H), 7.71 (d, J=1.2 Hz, 1H), 7.07-6.96 (m, 2H), 6.56-6.45 (m, 2H), 4.13 (s, 1H), 3.80 (s, 2H), 3.60 (s, 2H). EI-MS m/z: 359 [M]$^+$.

Example 66

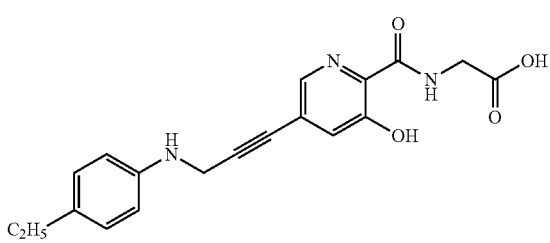 [SMILES: CCc1ccc(NCC#Cc2cnc(C(=O)NCC(=O)O)c(O)c2)cc1]

2-(3-Hydroxy-5-(3-p-ethylanilinopropyn-1-yl))picolinamido acetic acid

The preparation method is the same as that of Example 1, and propyne was replaced by 3-p-ethylanilinopropyne (174.9 mg, 1.1 mmol). Accordingly, a white solid product was obtained (68.0 mg, yield of two steps: 19.2%). m.p. 145.1-147.3° C. $^1$H NMR (300 MHz, DMSO-$d_6$) δ 8.70 (d, J=1.3 Hz, 1H), 8.20 (s, 1H), 7.64 (d, J=1.2 Hz, 1H), 6.99-6.90 (m, 2H), 6.63-6.53 (m, 2H), 4.11 (s, 1H), 3.80 (s, 2H), 3.60 (s, 2H), 2.64-2.5 (m, 2H), 1.19 (t, J=6.6 Hz, 3H). EI-MS m/z: 353 [M]$^+$.

Example 67

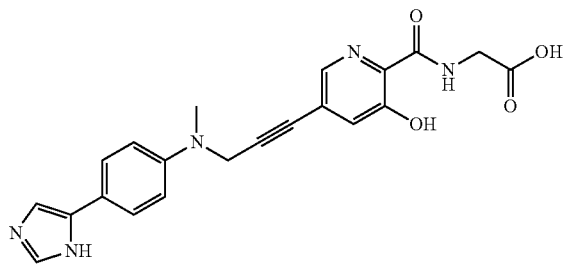 [SMILES: CN(CC#Cc1cnc(C(=O)NCC(=O)O)c(O)c1)c1ccc(-c2cnc[nH]2)cc1]

2-(3-Hydroxy-5-(3-((N-methyl-N-p-imidazol-2-ylphenyl)amino)propyn-1-yl))picolinamido acetic acid The preparation method is the same as that of Example 1, and propyne was replaced by 3-((N-methyl-N-p-imidazol-2-ylphenyl)amino)propyne (131.2 mg, 1.1 mmol). Accordingly, a white solid product was obtained (68.0 mg, yield of two steps: 16.7%). m.p. 199.1-201.7° C. $^1$H NMR (300 MHz, DMSO-$d_6$) δ 8.49 (d, J=1.3 Hz, 1H), 8.20 (s, 1H), 7.91 (s, 1H), 7.65-7.53 (m, 3H), 7.41 (s, 1H), 6.97-6.86 (m, 2H), 4.09 (s, 2H), 3.60 (s, 2H), 2.97 (s, 3H). EI-MS m/z: 405 [M]$^+$.

Example 68

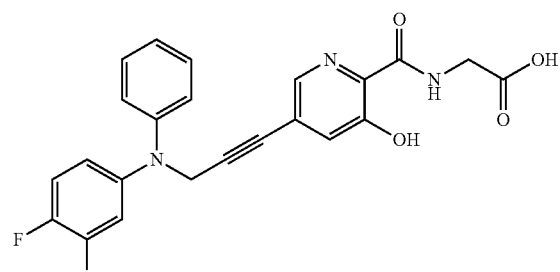

2-(3-Hydroxy-5-(3-((N-phenyl-N-3,4-difluorophenyl)amino)propyn-1-yl))picolinamido acetic acid The preparation method is the same as that of Example 1, and propyne was replaced by 3-((N-phenyl-N-3,4-difluorophenyl)amino)propyne (267.3 mg, 1.1 mmol). Accordingly, a white solid product was obtained (72.0 mg, yield of two steps: 16.4%). m.p. 205.2-207.3° C. $^1$H NMR (300 MHz, DMSO-$d_6$) (8.80 (d, J=1.2 Hz, 1H), 8.20 (s, 1H), 7.63 (d, J=1.3 Hz, 1H), 7.30-7.17 (m, 4H), 7.11-6.96 (m, 1H), 6.93-6.90 (m, 1H), 6.79-6.76 (m, 1H), 6.66-6.56 (m, 1H), 3.80 (s, 2H), 3.60 (s, 2H). EI-MS m/z: 437 [M]$^+$.

Example 69

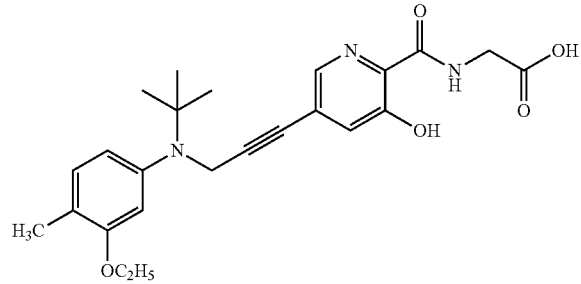 [SMILES: CCOc1cc(N(CC#Cc2cnc(C(=O)NCC(=O)O)c(O)c2)C(C)(C)C)ccc1C]

2-(3-Hydroxy-5-(3-((N-tert-butyl-N-3-ethoxy-4-methylphenyl)amino)propyn-1-yl))picolinamido acetic acid The preparation method is the same as that of Example 1, and propyne was replaced by 3-((N-tert-butyl-N-3-ethoxy-4-methylphenyl)amino)propyne (269.5 mg, 1.1 mmol). Accordingly, a white solid product was obtained (82.0 mg, yield of two steps: 18.6%). m.p. 210.2-212.6° C. $^1$H NMR (300 MHz, DMSO-$d_6$) δ 8.62 (d, J=1.3 Hz, 1H), 8.20 (s, 1H), 7.37 (d, J=1.2 Hz, 1H), 6.99-6.96 (m, 1H), 6.54 (s, 1H), 6.58-6.48 (m, 1H), 4.09 (s, 3H), 4.07 (s, 1H), 3.60 (s, 2H), 2.23 (d, J=1.0 Hz, 3H), 1.43 (t, J=5.9 Hz, 3H), 1.22 (s, 10H). EI-MS m/z: 439 [M]$^+$.

What is claimed is:

1. A compound of formula (I) or a pharmaceutically acceptable salt thereof:

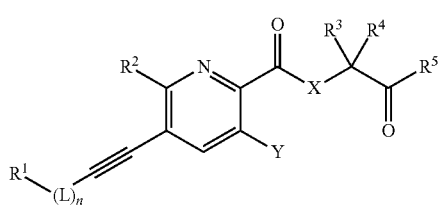

wherein X represents NH, NCH$_3$ or CH$_2$;
Y represents hydrogen, hydroxy, methoxy or ethoxy;
L represents —CH$_2$—, —CH$_2$O— or

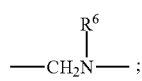

$R^6$ represents hydrogen, C$_1$-C$_4$ alkyl or phenyl;
n represents 1;
$R^1$ represents C$_1$-C$_4$ alkyl, phenyl, quinolinyl, benzofuranyl, naphthyl, substituted phenyl, 5- to 6-membered heteroaryl containing oxygen or nitrogen, or substituted 5- to 6-membered heteroaryl containing oxygen or nitrogen, wherein the substituent is C$_1$-C$_4$ alkyl, C$_1$-C$_4$ alkoxy, C$_1$-C$_4$ haloalkyl, halogen, cyano,

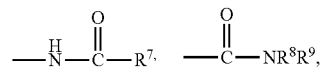

phenyl or 5- to 6-membered heteroaryl containing oxygen or nitrogen, wherein $R^7$ represents C$_1$-C$_4$ alkyl; $R^8$ and $R^9$ each independently represent hydrogen or C$_1$-C$_4$ alkyl, or $R^8$ and $R^9$ are attached to form a 3- to 7-membered heterocyclyl containing nitrogen;

$R^2$ represents hydrogen, halogen or methyl;

$R^3$ and $R^4$ each independently represent hydrogen, methyl or ethyl; and $R^5$ represents hydroxy, C$_1$-C$_4$ alkoxy, cyclopropoxy, or —NR$^{10}$R$^{11}$, wherein R$^{10}$ and R$^{11}$ each independently represent hydrogen, methyl or ethyl.

2. The compound or the pharmaceutically acceptable salt thereof according to claim 1, wherein X represents NH.

3. The compound or the pharmaceutically acceptable salt thereof according to claim 1, wherein L represents —CH$_2$—, —CH$_2$— or

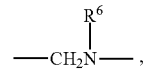

and $R^6$ represents hydrogen, methyl, tert-butyl or phenyl.

4. The compound or the pharmaceutically acceptable salt thereof according to claim 1, wherein $R^1$ represents substituted phenyl, wherein the substituent is methyl, ethyl, isopropyl, tert-butyl, methoxy, tert-butoxy, phenyl, cyano, halogen, fluoromethyl, trifluoromethyl, imidazolyl, acetylamino, or

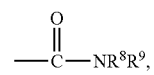

wherein $R^8$ and $R^9$ each independently represent hydrogen, methyl, butyl or tert-butyl, or $R^8$ and $R^9$ are attached to form aziridinyl, tetrahydropyrrolyl or N-methylhomopiperazinyl.

5. The compound or the pharmaceutically acceptable salt thereof according to claim 1, wherein $R^1$ represents phenyl, naphthyl, quinolinyl or benzofuranyl.

6. The compound or the pharmaceutically acceptable salt thereof according to claim 1, wherein $R^3$ or $R^4$ represents hydrogen.

7. The compound or the pharmaceutically acceptable salt thereof according to claim 1, wherein $R^5$ represents —NH$_2$, —NHCH$_3$, hydroxy, methoxy, isopropoxy, or cyclopropoxy.

8. A pharmaceutical composition, comprising the compound or the pharmaceutically acceptable salt thereof according to claim 1, and a pharmaceutically acceptable carrier.

9. A compound of formula (I) or a pharmaceutically acceptable salt thereof:

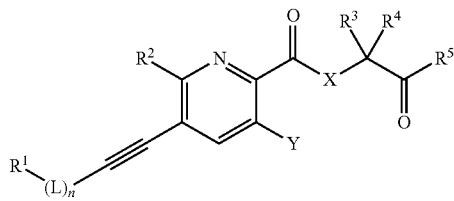
wherein X represents NH, Y represents hydroxy, $R^2$, $R^3$ and $R^4$ represent hydrogen, $R^5$ represents hydroxy or $C_1$-$C_4$ alkoxy, L represents —$CH_2$— or —$CH_2$—, n represents 0 or 1, and $R^1$ represents substituted phenyl, wherein the substituent is $C_1$-$C_4$ alkyl, $C_1$-$C_4$ alkoxy or halogen.
10. A compound selected from the group consisting of:
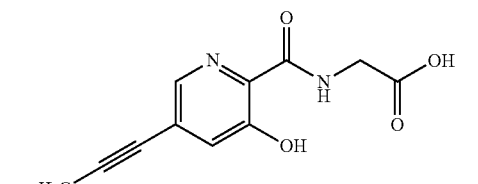
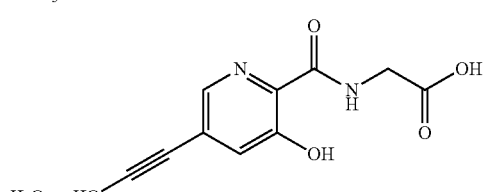
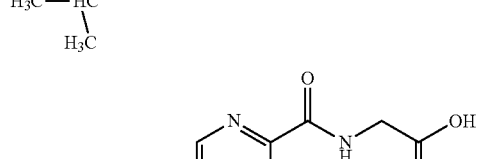
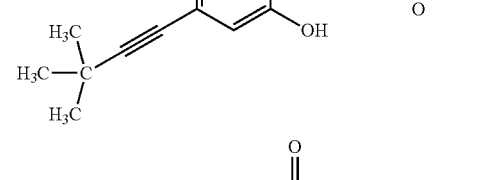
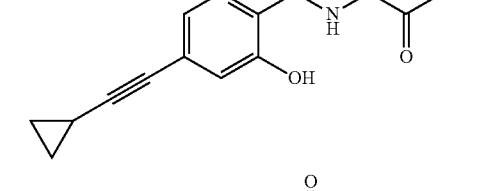
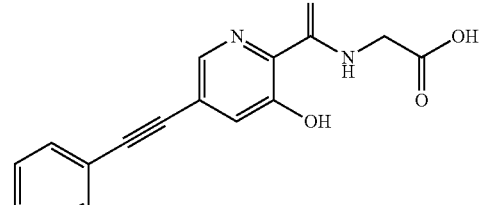
-continued
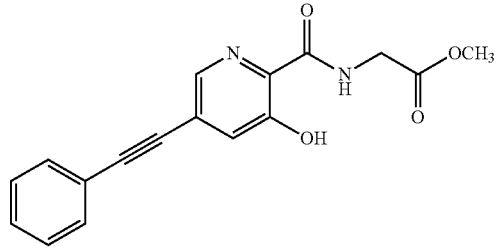
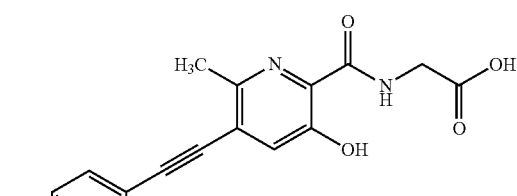
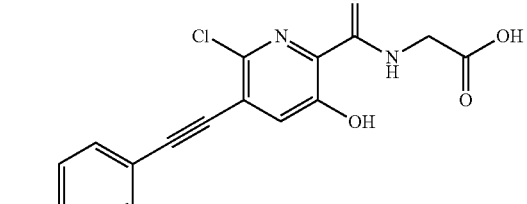
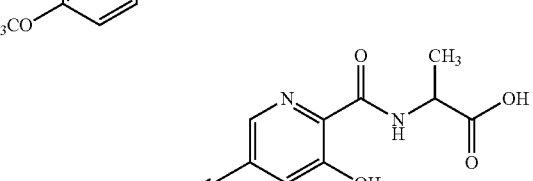

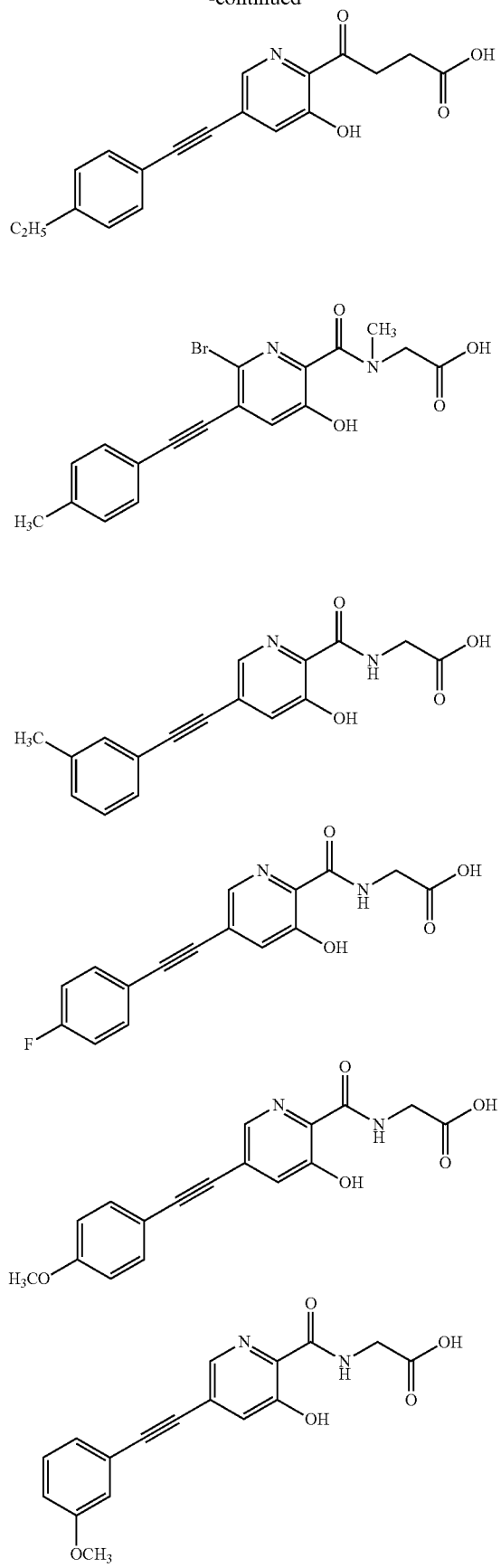
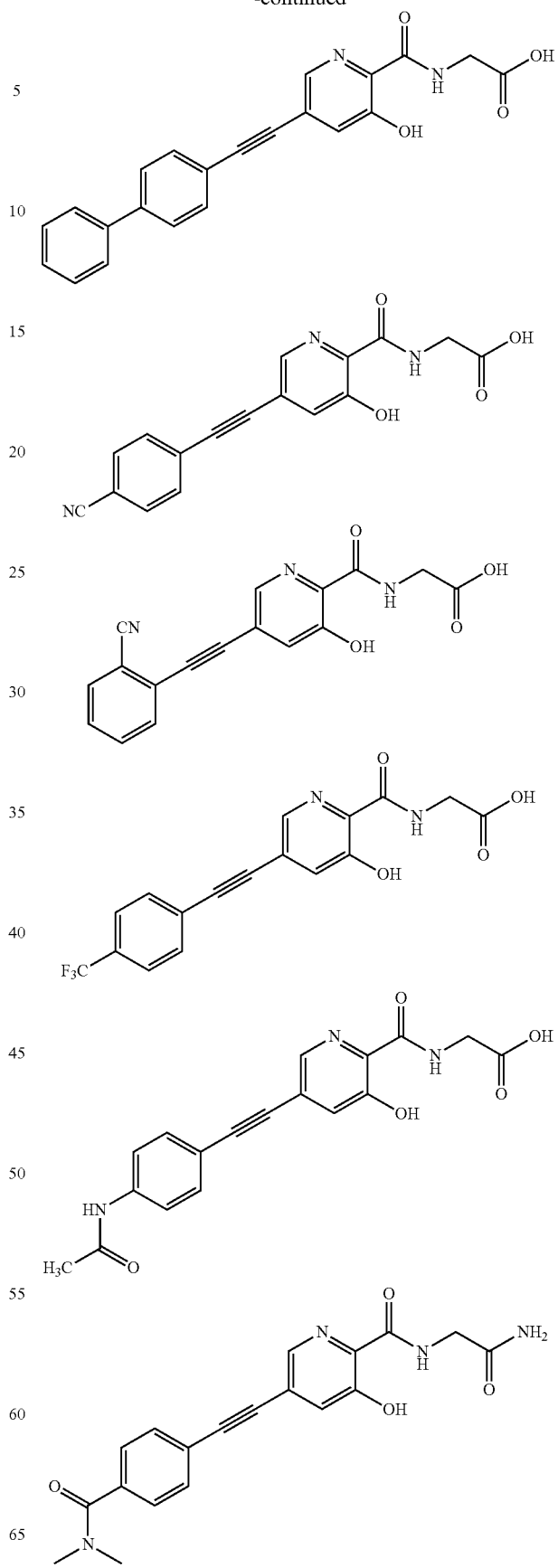

-continued

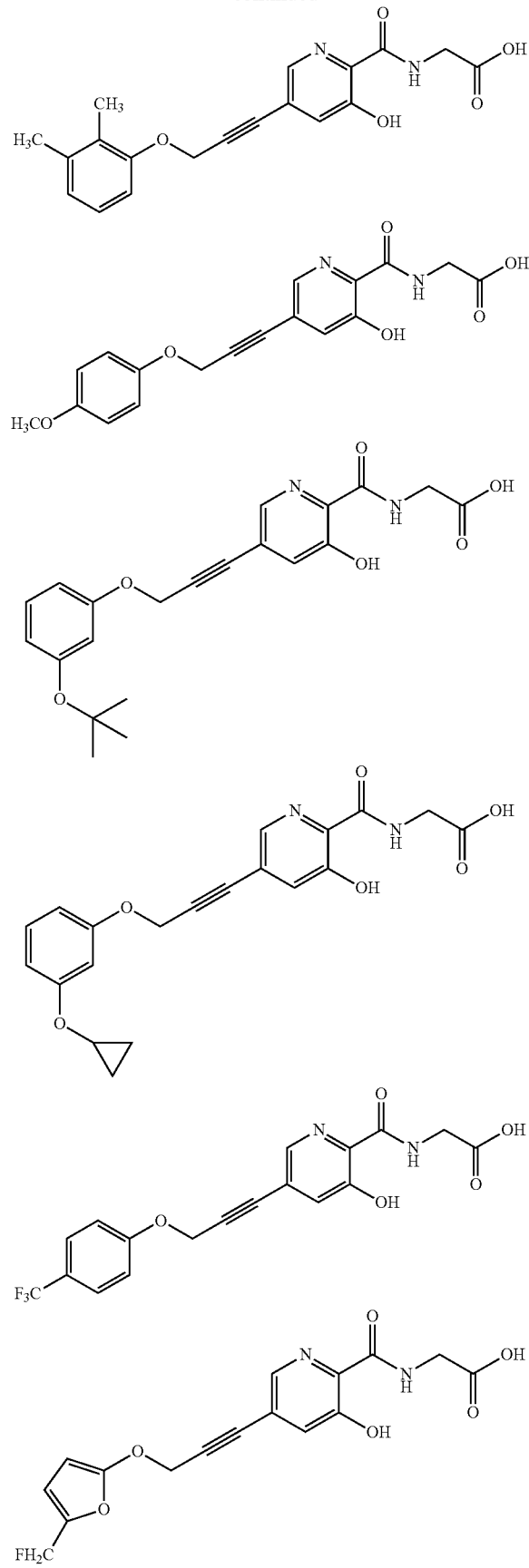
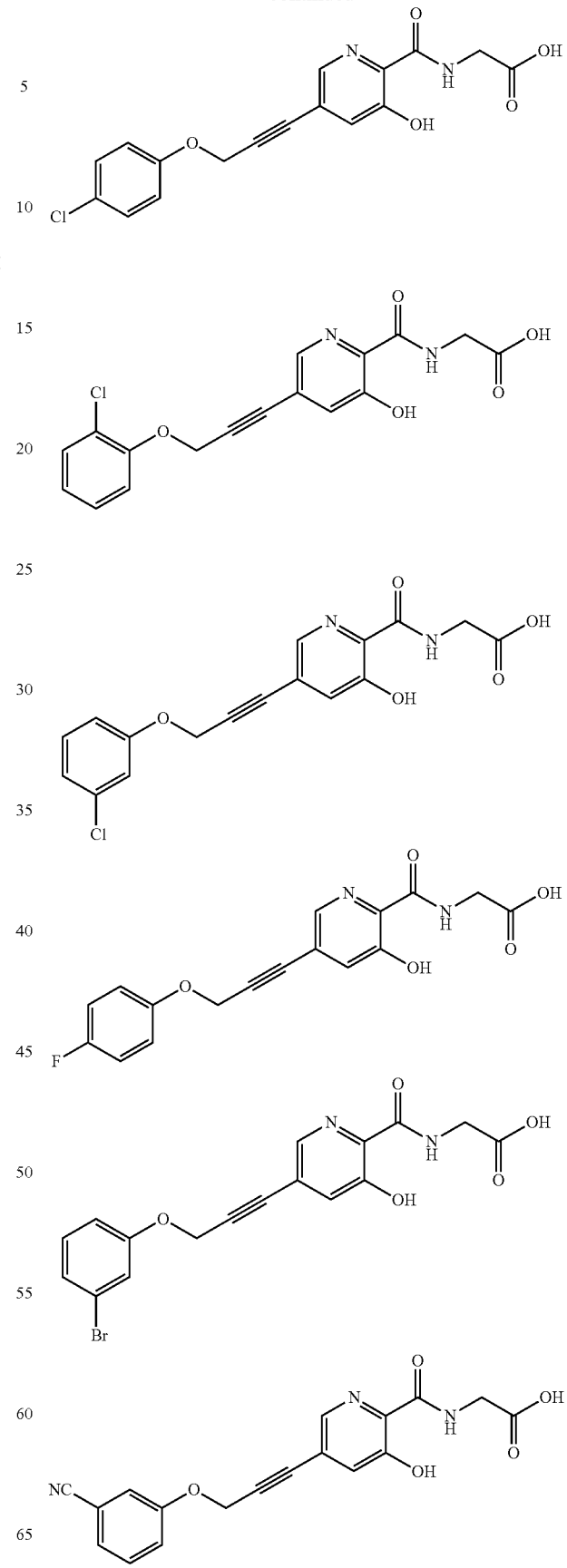

53
-continued
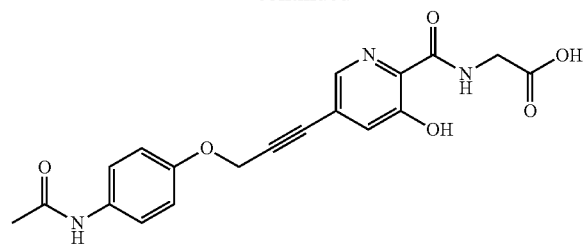
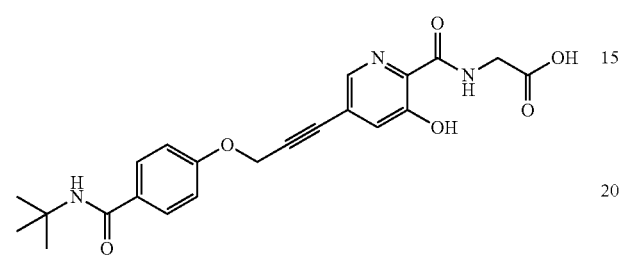
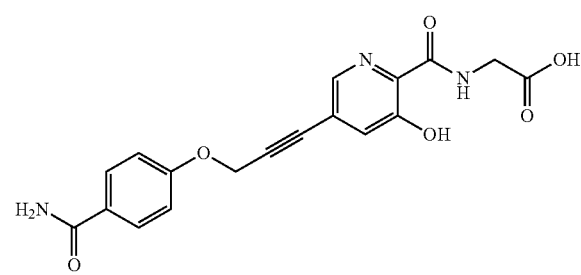
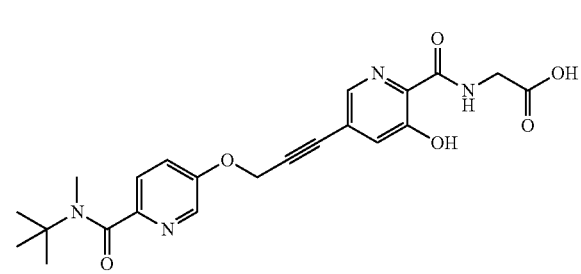
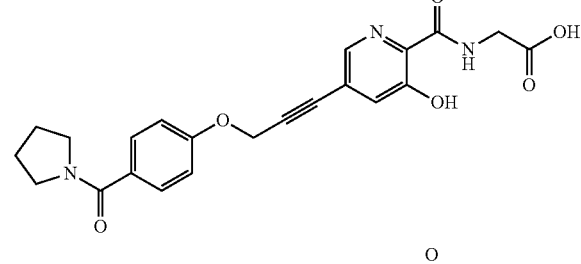
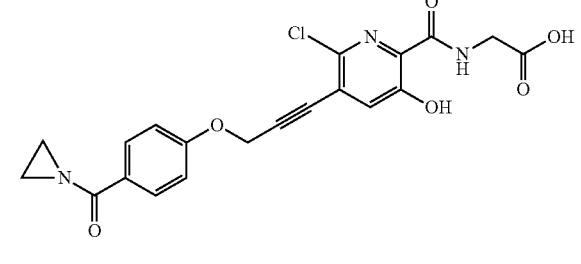
54
-continued
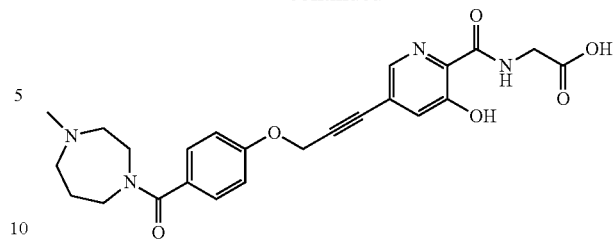
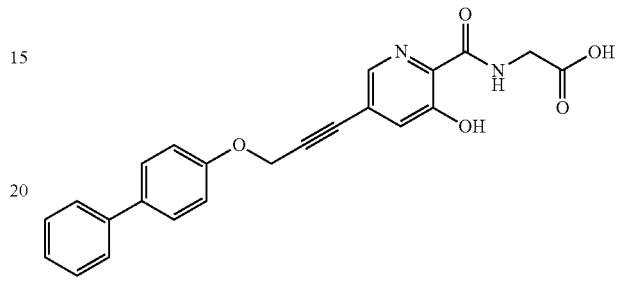
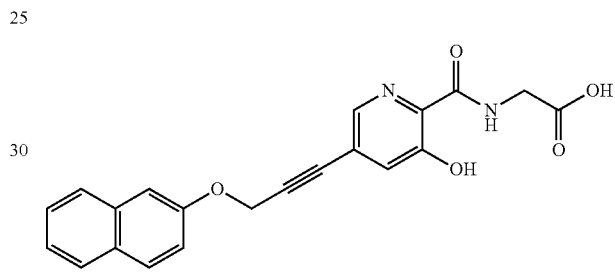
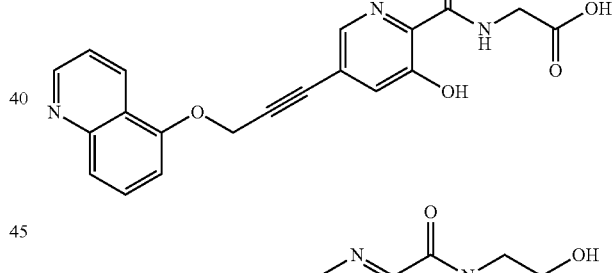
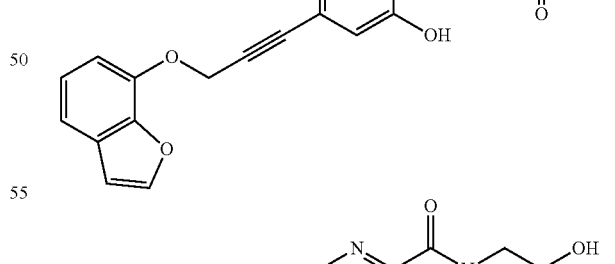
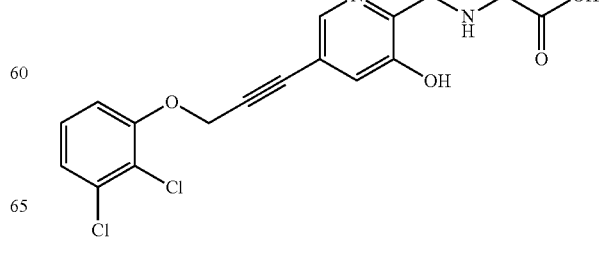

-continued

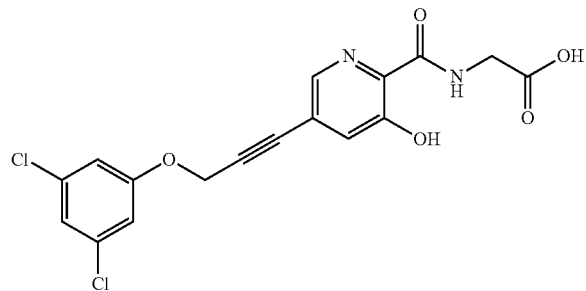

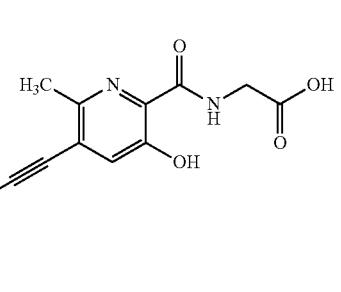

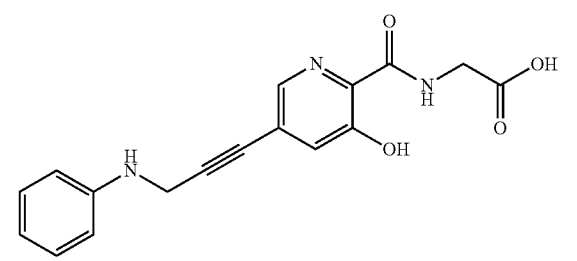

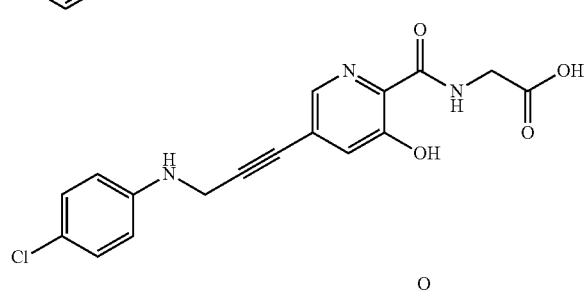

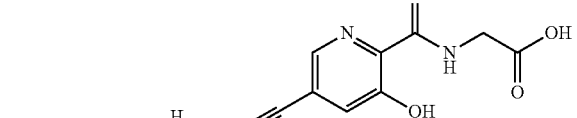

-continued

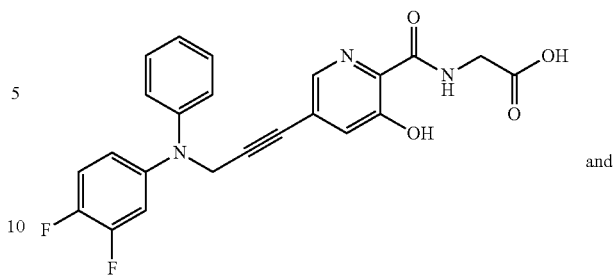

and

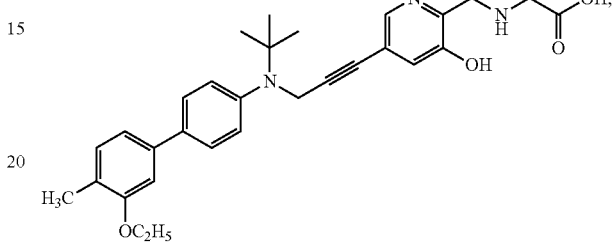

or a pharmaceutically acceptable salt thereof.

11. A method for preparing the compound or the pharmaceutically acceptable salt thereof according to claim 1, wherein the compound is a compound of formula (I-a), comprising coupling a compound of formula (VI) with a compound of formula (VII) in the presence of a catalyst to obtain the compound of formula (I-a):

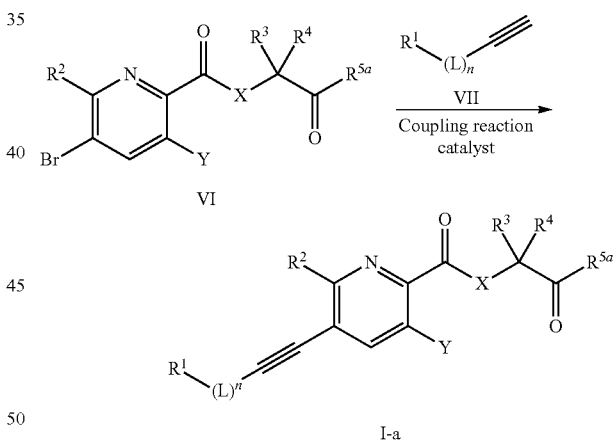

wherein $R^1$, $R^2$, $R^3$, $R^4$, X, Y, n and L are as defined in claim 1; and $R^{5a}$ represents $C_1$-$C_4$ alkoxy or —$NR^{10}R^{11}$, wherein $R^{10}$ and $R^{11}$ each independently represent hydrogen, methyl or ethyl.

12. A method for preparing the compound or the pharmaceutically acceptable salt thereof according to claim 1, wherein the compound is a compound of formula (I-b), comprising:

(i) coupling a compound of formula (VI) with a compound of formula (VII) in the presence of a catalyst to obtain a compound of formula (I-a); and (ii) hydrolyzing the compound of formula (I-a) to obtain the compound of formula (I-b):

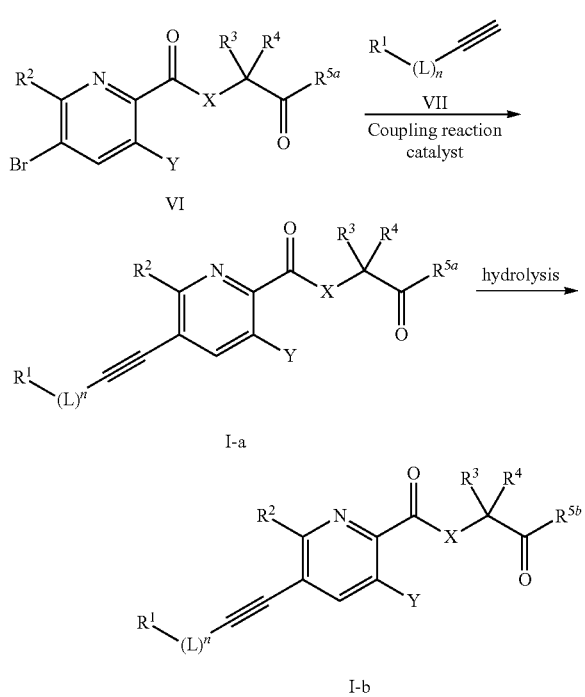

wherein $R^1$, $R^2$, $R^3$, $R^4$, X, Y, n and L are as defined in claim 1; and $R^{5b}$ represents hydroxy.

13. A pharmaceutical composition, comprising the compound or the pharmaceutically acceptable salt thereof according to claim 10, and a pharmaceutically acceptable carrier.

14. A method for inhibiting prolyl hydroxylase in a subject in need thereof, comprising administering to the subject the pharmaceutical composition according to claim 8.

15. A method for inhibiting prolyl hydroxylase in a subject in need thereof, comprising administering to the subject the pharmaceutical composition according to claim 13.

16. The compound of claim 10, wherein the compound is:

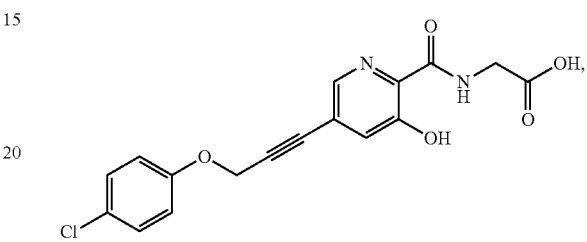

or a pharmaceutically acceptable salt thereof.

17. A pharmaceutical composition, comprising the compound or the pharmaceutically acceptable salt thereof according to claim 16, and a pharmaceutically acceptable carrier.

* * * * *